US007906701B2

(12) United States Patent
Hasegawa et al.

(10) Patent No.: US 7,906,701 B2
(45) Date of Patent: Mar. 15, 2011

(54) P300 TRANSGENIC ANIMAL

(75) Inventors: Koji Hasegawa, Kyoto (JP); Yosuke Kawase, Shizuoka (JP); Hiroshi Suzuki, Shizuoka (JP)

(73) Assignees: Koji Hasegawa, Kyoto (JP); Chugai Seiyaku Kabushiki Kaisha, Tokyo (JP)

( * ) Notice: Subject to any disclaimer, the term of this patent is extended or adjusted under 35 U.S.C. 154(b) by 27 days.

(21) Appl. No.: 11/827,438

(22) Filed: Jul. 11, 2007

(65) Prior Publication Data
US 2009/0083863 A1 Mar. 26, 2009

Related U.S. Application Data

(63) Continuation of application No. 10/332,966, filed as application No. PCT/JP01/06086 on Jul. 13, 2001, now abandoned.

(30) Foreign Application Priority Data

Jul. 14, 2000 (JP) .................... 2000-215143

(51) Int. Cl.
*G01N 33/00* (2006.01)
*A01K 67/00* (2006.01)
*A01K 67/027* (2006.01)
(52) U.S. Cl. ................ 800/3; 800/13; 800/18
(58) Field of Classification Search ........ 800/3, 13, 800/18
See application file for complete search history.

(56) References Cited

OTHER PUBLICATIONS

Kappel et al., 1992, Current Opinion in Biotechnology, vol. 3, p. 548-553.*
Wall, R. J., 1996, Theriogenology, vol. 45, p. 45-68.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Rudinger, 1976, Peptide Hormones, Parsons, University Park Press, Baltimore, p. 1-7.
Kaye, et al., 1990, Proc. Natl. Acad. Sci. USA, vol. 87, pp. 6922-6926.
Skolnick et al., 2000, Trends in Biotech, vol. 18, pp. 34-39.
Yanazume, Tetsuhiko et al., "Cardiac p300 Is Involved in Myocyte Growth with Decompensated Heart Failure", Molecular and Cellular Biology, May 2003, p. 3593-3606, vol. 23, No. 10.

Gusterson, Rosalind J., et al., "The Transcriptional Co-Activators CREB-Binding Protein (CBP) and p300 Play a Critical Role in Cardiac Hypertrophy That is Dependent on Their Histone Acetyltransferase Activity", J. Biol. Chem., vol. 278, No. 9, Feb. 26, 2003, pp. 6636-6647.
Matthew, Sumy et al., "A Ternary Complex of Transcription Factors, Nished and NFATc4, and Co-activator p300 bound to an Intronic Sequence, Intronic Regulatory Element, Is Pivotal for the Up-regulation of Myosin Light Chain-2v Gene in Cardiac Hypertrophy", The Journal of Biological Chemistry, vol. 279, No. 39, Issue of Sep. 24, pp. 41018-41027, 2004.
Gen Fujii, Remi Tsuchiya, Yuzuru Itoh, Kosuke Tashiro, Setsuo Hirohashi, Molecular Cloning and expression of *Xenoptis* p200/CBP, Biochimica et Biophysica Acts 1443 (1998).
Tso-Pang Yao, Suk P. Oh, Miriam Fuchs, Nai-Dong Zhou, Lian-Ee ch'ng, David Newsome, Roderick T. Bronson, En Li, David M. Livingson., and Richard Eckner, Gene Dosage-Dependent Embryonic Development and Proliferation Defects in Mice Lacking the Transcriptional Integrator, Cell, vol. 93, PR, 361-372, May 1, 1998.
Hasegawa, Kouji, et al., "Kouketsuatsu-sei Shinhidai kara Shinfuzen e no Ikou ni okeru Shinkin ET-1 no Tensha Chousetsu Kikou: p300-GATA Keiro no Yakuwari" (The transcription regulation mechanism of myocardial ET-1 in the trnansition from hypertensive cardiac hypertrophy to heart failure: the role of p300-GATA pathway), Ketsuatsu, 1999, vol. 6, No. 7, pp. 665-669.
Hasegawa, Kouji, et al., "Transcriptional Coactivator p300 Stimulates Cell Type-specific Gene Expression in Cardiac Myocytes.", J.Biol.Chem, 1997. vol. 2721, No. 32. pp. 20049-20054.
Kakita, T., et al., "A p300 Protein Is Involved in α1-Adrener-gic Agonist-stimulated Endothelin-1 Transcription in Cardiac Myocytes as a Coactivator of GATA-4/5.", Circulation, 1999, vol. 100, No. 18, Suppl. I, pp. 213.1105.
Subramaniam, A., et al., "Tissue-specific Regulation of the α-Myosin Heavy Chain Gene Promoter in Transgenic Mice", J.Biol.Chem., 1991, vol. 266, No. 36, pp. 24613-24620.
Kakita, T., et al., "p300 Protein as a Coactivator of GATA-5 in the Transcription of Cardiac-restricted Atrial Natriuretic Factor Gene", J.Biol.Chem., 1999, vol. 274, No. 48, pp. 34096-34102.
Kakita, T., et al., "A nuclear Complex of PPAR/p300 Is Markedly Down-regulated in Hypertrophied Rat Left Ventricular Myocardium with Normal Systolic Function." Circulation, 1999, vol. No. 18, Suppl. I, pp. 214, 1106.
Kakita, T., at al., "Overexpression of p300 is Sufficient to Induce Cardiac Endothelin-1 Expression and Hypertrophy in Vivo." Circulation, 2000, vol. 102, No. 18, Suppl. II, pp. 223.
The International Search Report and International Preliminary Examination Report issued in corresponding International Application PCT/JP01/06086.

* cited by examiner

*Primary Examiner* — Shin-Lin Chen
(74) *Attorney, Agent, or Firm* — Davidson, Davidson & Kappel, LLC

(57) ABSTRACT

The present invention relates to a transgenic animal wherein DNA encoding p300 and a promoter exerting its activity in myocardial cells are introduced, and a screening method using the same.

4 Claims, 7 Drawing Sheets

FIG. 2  Heart-specific expression of the introduced p300 gene in the transgenic mouse

FIG. 5

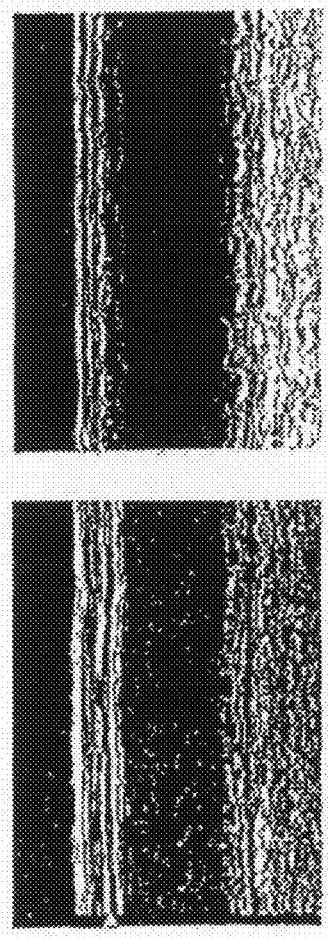

|  | 2-month old wild type (WT) | 2-month old transgenic (TG) | 6-month old wild type (WT) | 6-month old transgenic (TG) |
|---|---|---|---|---|
| Left ventricular end-diastolic dimension: LVDd (mm) | 3.00 ± 0.05 | 2.73 ± 0.37 | 2.85 ± 0.13* | 5.64 ± 0.42* |
| Left ventricular end-systolic dimension: LVDs (mm) | 1.13 ± 0.09 | 1.23 ± 0.03 | 0.93 ± 0.08* | 4.96 ± 0.60* |
| Left ventricular fractional shortening: %FS | 62.2 ± 2.8 | 57.1 ± 6.1 | 67.7 ± 1.6* | 13.3 ± 4.6* |
| Interventricular septum thickness: IVST (mm) | 0.80 ± 0.10 | 0.77 ± 0.05 | 0.80 ± 0.09 | 0.82 ± 0.08 |
| Left ventricular posterior wall thickness: LVPWT (mm) | 0.83 ± 0.19 | 0.93 ± 0.08 | 1.03 ± 0.16 | 0.82 ± 0.12 |
| Heart rate: HR (beat/min) | 626 ± 24 | 643 ± 24 | 656 ± 29 | 571 ± 35 |

*: p<0.005

P300 TRANSGENIC ANIMAL

TECHNICAL FIELD

The present invention relates to an animal into which DNA encoding p300 (hereinafter referred to as "p300 gene") is introduced so as to be expressed in myocardial cells, and a screening method using the same animal.

BACKGROUND ART

The heart is an organ with the unique function of continually repeated contraction and relaxation. Myocardial cells, which are the main components of the heart, maintain division potential after differentiation, and keep actively dividing and proliferating during the prenatal period. However, they lose their division potential at the time of birth, and thereafter the growth of the heart is dependent on the growth in size of individual myocardial cells (physiological hypertrophy).

There are some cases wherein the heart responds to various stimuli such as hypertension thereby growing in size more than it would physiologically, and this is called in general cardiac hypertrophy. Cardiac hypertrophy is a compensatory mechanism having a limitation and does not reduce contraction function of the heart in itself. However, a high hypertrophy exceeding the limitation causes biochemical changes in the myocardial cells, so that the heart suffers contraction dysfunction (heart failure).

There have been already some reports on the onset mechanism of heart failure. For example, Hasegawa et al. reported that GATA transcription factors played an important role in intracellular signal transduction at the onset of heart failure (Hasegawa K et al.: Circulation 1997; 96:3943-3953). Morimoto et al. reported that among the GATA transcription factors, GATA-5 played a particularly important role (Morimoto T et al.: J. Biol. Chem. 1999; 274:12811-12818). Further, Iwanaga et al. reported that the expression enhancement of endothelin-1 in cardiac muscle played an important role in the development from compensatory cardiac hypertrophy caused by hypertension to heart failure (Iwanaga Y et al.: Circulation 1998; 98:2065). Furthermore, Hasegawa et al. reported that p300, which is an adenovirus E1A binding protein, functioned as a co-activator of GATA-5 (Hasegawa Koji et al.: Blood Pressure vol. 6 1999:665-669). Meanwhile, Kanai et al. confirmed that p300 induced apoptosis in myocardial cells (Presentation, the 63th Annual Scientific Meeting of the Japanese Circulation Society, Mar. 27, 1999-Mar. 29, 1999), and also suggested that there is a possibility that p300 works to suppress cardiac hypertrophy. Thus, the relation between p300 and cardiac hypertrophy is not clear.

Although the onset mechanism of heart failure is gradually being revealed as described above, there are many points which have not sufficiently been unraveled yet. One reason for this lag in the research is the fact that experimental animals to be models of heart failure have not been developed yet.

DISCLOSURE OF THE INVENTION

The present invention has been made against this technical background, and an object of the present invention is to provide a model animal to be affected by heart failure, which is useful to elucidate the onset mechanism of heart failure.

The present inventors have focused their attention on p300 from among various factors associated with the onset of heart failure, and found it possible to develop a pathology nearly identical to heart failure by introducing a p300 gene into an animal. They have accomplished the present invention based on this finding.

Namely, the present invention is a transgenic animal wherein a p300 gene and a promoter exerting its activity in myocardial cells are introduced.

Further, the present invention is a screening method of a substance having therapeutic activity for heart failure, which comprises the following steps:
(1) administering a test substance to the transgenic animal; and
(2) confirming whether cardiac hypertrophy is suppressed or not in the transgenic animal.

Furthermore, the present invention is a substance obtained by the above screening method.

Moreover, the present invention is a heart failure therapeutic agent containing as an active component a substance obtained by the above screening method. The transgenic animal of the present invention has the feature that a p300 gene and a promoter exerting its activity in myocardial cells are introduced.

Hereinafter, the present invention will be described in detail.

The transgenic animal of the present invention is characterized by that a p300 gene and a promoter exerting its activity in myocardial cells are introduced thereinto.

The animal may be any kind of animal except human, but preferable examples of the animal include mice, rats, rabbits, miniature pigs, and pigs.

As a p300 gene, for example, p300 gene (SEQ ID NO:1) derived from human can be used, but any p300 genes other than this may be used.

As long as a promoter to be introduced has activity in myocardial cells and increases its activity as the animal grows, it is not particularly limited. As a preferable promoter, α-myosin heavy chain promoter (SEQ ID NO:2) may be noted. This promoter shows low activity during the prenatal period and increases its activity as the animal grows. Accordingly, it is possible by using this promoter to prevent the animal from developing heart failure and dying at a stage when the animal is not sufficiently matured.

The transgenic animal of the present invention can be, for example, produced as follows.
(1) A vector carrying a p300 gene and a promoter exerting its activity in myocardial cells is prepared. A p300 gene derived from a human can be prepared based on the sequence described in SEQ ID NO:1. Further, the sequences of other p300 genes are open to the public in GenBank managed by the National Center for Biotechnology Information, USA. Thus, based on these sequences, the p300 gene can be prepared. α-myosin heavy chain promoter which is one of the promoters having activity in myocardial cells can be prepared based on the sequence described in SEQ ID NO:2. The p300 gene and the promoter exerting its activity in myocardial cells, both prepared as above, are inserted into a commercially available vector, e.g. pBluescript II, thereby preparing a target vector.
(2) An expression cassette is excised from the prepared vector and introduced into a totipotent cell. As the totipotent cell, a fertilized egg, an early embryo, an ES cell, etc. can be used. The introduction of the expression cassettes into the totipotent cells can be performed by the electrostatic pulse method, liposome method, calcium phosphate method, microinjection method, etc.
(3) The above treated totipotent cells are transferred into the oviducts of pseudopregnant recipients. Then, offspring are born, and from among them, individuals having foreign p300 genes are selected. Whether or not an individual has a foreign p300 gene is determined by Southern blotting or PCR using a probe or primer specific to the foreign p300 gene. An individual having the foreign p300 gene shows higher level of expression of p300 gene than an individual having only endogenous genes, and thus it is possible to determine the above, based on the difference in expression level.

The transgenic animal of the present invention shows pathologies specific to heart failure such as cardiac hypertrophy or excessive synthesis of endothelin-1 in the heart muscle, and therefore it can be used as a model animal for heart failure.

Further, a test substance is administered to the transgenic animal of the present invention, and thereafter the screening of substances having therapeutic activity for heart failure can be performed by confirming whether or not cardiac hypertrophy is suppressed in this animal.

The test substance is not particularly limited, but examples thereof include peptides, proteins, nonpeptidic compounds, synthetic compounds, and fermented products, cell extracts.

The administration means of the test substance is not particularly limited, but oral administration, injection administration, etc. are exemplified.

Whether or not cardiac hypertrophy is suppressed is determined by extirpating the heart of the transgenic animal to which the test substance is administered, measuring the weight of that heart, and then comparing that weight with the weight of the heart from the control (the transgenic animal to which the test substance is not administered). Further, the occurrence of cardiac hypertrophy can be confirmed by echocardiography, etc., and thus the occurrence of the suppression is determined. Furthermore, as cardiac hypertrophy occurs, excessive synthesis of atrial natriuretic peptides or expression of β-myosin heavy chain genes is observed. Accordingly, these can be used as indices for determining the occurrence of the suppression. It is noted that the expression of β-myosin heavy chain genes is confirmed by the method of Hasegawa et al. (Hasegawa K et al., Circulation 1977:96: 3943-3953). In addition to these methods, the occurrence of the suppression of cardiac hypertrophy may be determined by mortality rate, because there is a high probability that the transgenic animal of the present invention develops heart failure unless cardiac hypertrophy is suppressed, thereby leading to death.

Since the substance obtained by the above screening method has therapeutic activity for heart failure, the substance is formulated by a known pharmaceutical production method and can be used as a therapeutic or preventive agent for heart failure.

BRIEF DESCRIPTION OF THE DRAWINGS

FIG. 5 shows M-mode echocardiography carried out in Example 6, and each measurement value.

This specification includes the contents as disclosed in the specification of Japanese Patent Application No. 2000-215143, which is a priority document of the present application.

BEST MODE FOR CARRYING OUT THE INVENTION

Example 1

Figure 1:
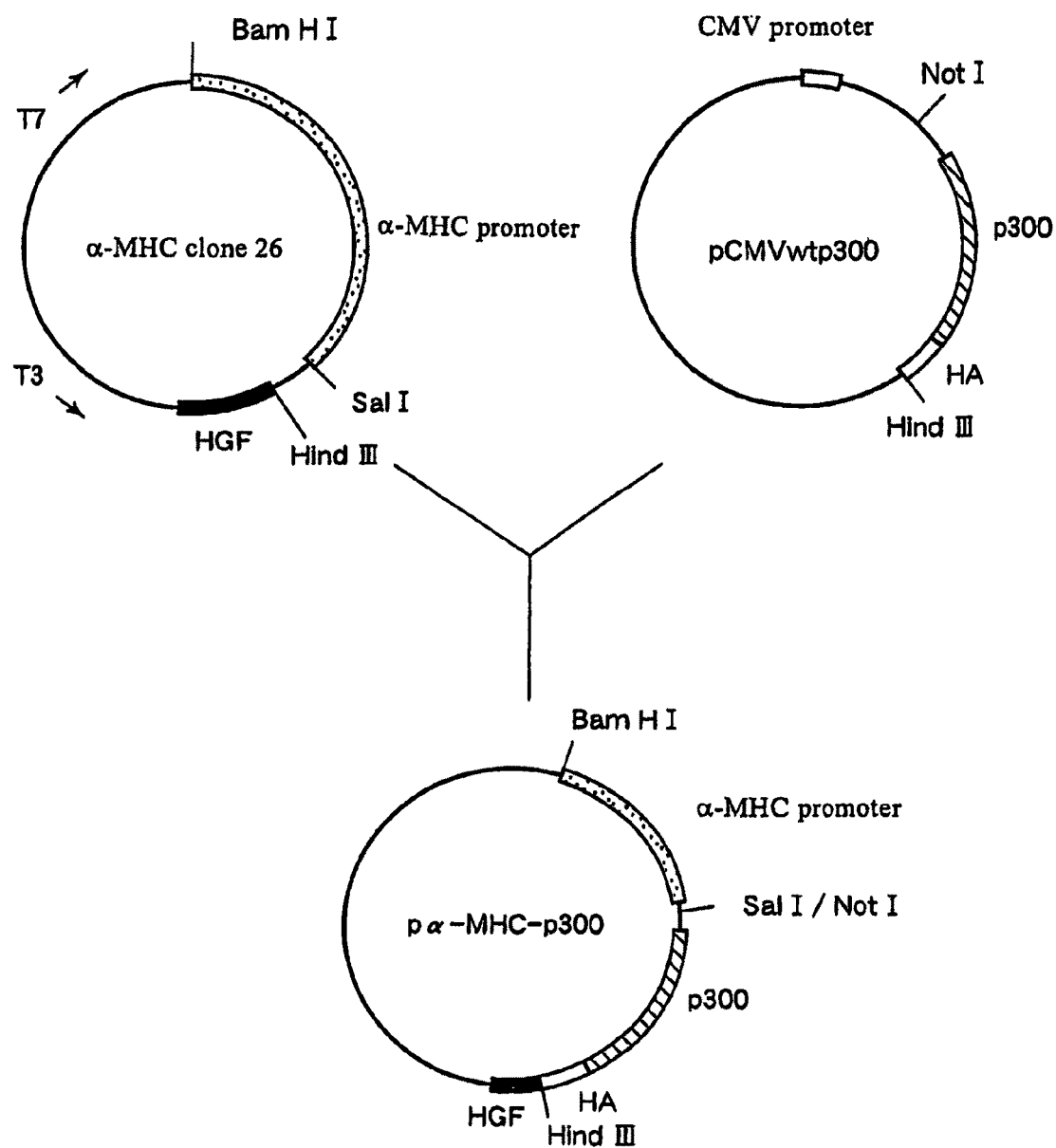
FIG. 1 shows the structures of pCMVwtp300, α-MHC clone 26, and pα MHC-p300.

A pCMVwtp300 was treated with NotI and HindIII, a fragment carrying a p300 gene was excised, and thereafter NotI restriction site of this fragment was blunted. Meanwhile, α-MHC Clone 26 (accession no. U71441) carrying an α-myosin heavy chain promoter (αMHC promoter) was treated with SalI and HindIII, and thereafter SalI restriction site was blunted and the above described fragment carrying the p300 gene (Eckner, R. et al.: Genes Dev. 1994:8:869-884, accession no. U01877) was inserted into this restriction site. Then, pαMHC-p300 carrying αMHC promoter and the p300 gene were prepared. The structures of pCMVwtp300, α-MHC Clone26, and pαMHC-p300 are shown in FIG. 1. It is noted that pCMVwtp300 and α-MHC Clone26 were furnished from Drs. Richard Eckner and David M. Livingston (Harvard Medical School, Boston, Mass.) and Robbins, J. (Molecular Card. Biol., Children's Hospital, Cincinnati, Ohio), respectively.

pαMHC-p300 was digested by NotI and a fragment carrying αMHC promoter and p300 gene was excised. After adjusting the concentration of this DNA fragment to 3 ng/μl, the DNA fragment was injected into a frozen-thawed pronuclear stage fertilized egg, which had been taken from a C57BL/6J strain mouse (Clea Japan, Inc.) and cryopreserved. The injection of the DNA into the fertilized egg was performed by microinjection method (Ueda Otoya et al.: Latest Technology of Gene Targeting: 2000:190-207). Among 319 fertilized eggs to which the DNAs were injected, 236 eggs survived and, of those, 199 were differentiated to 2-cell embryos. These 2-cell embryos were transferred into the oviducts of pseudopregnant recipient mice (ICR strain, Clea Japan, Inc.) that had been made pseudopregnant in advance. 54 offspring were obtained. The obtained offspring were checked using the Southern blotting method for whether or not they had the αMHC promoter and p300 gene. As a probe, a DNA fragment was used, which is amplified by PCR using pαMHC-p300 as a template and the following primers.

```
Sense primer:
TCTTAGCAAACCTCAGGCAC    (SEQ ID NO: 3)
(corresponding to 5230 to 5249 of SEQ ID NO: 2)

Antisense primer:
CCACCATTGGTTAGTCCCAA    (SEQ ID NO: 4)
(corresponding to 1356 to 1375 of SEQ ID NO: 1)
```

As a result of Southern blotting, it was confirmed that the objective DNA was contained in 6 individuals. Transgenic mice strains for 3 mice out of 6 individuals were established.

These three mice (21, 39, and 40 strains) were crossed with wild type of C57BL/6J mice to obtain the offsprings. Whether or not these offspring mice have the introduced gene was checked by the same Southern blotting method as described above. The following table shows sex of the offspring mice and the presence or absence of the introduced gene.

TABLE 1

| Parent Strain | Individual No. | Presence or absence of an introduced gene | Sex |
|---|---|---|---|
| 21 | 6 | Present | Female |
| | 5 | Present | Female |
| | 9 | Present | Male |
| | 1 | Present | Male |
| | 3 | Present | Male |
| | 7 | Present | Male |
| | 2 | Absent | Male |
| | 8 | Absent | Male |
| | 12 | Absent | Female |
| 39 | 34 | Present | Female |
| | 56 | Present | Male |
| | 20 | Present | Female |
| | 32 | Present | Male |
| | 36 | Present | Male |
| | 6 | Absent | Female |
| | 59 | Absent | Female |
| | 8 | Absent | Male |
| | 35 | Absent | Male |
| | 55 | Absent | Male |
| 40 | 61 | Present | Male |
| | 34 | Present | Female |
| | 51 | Present | Male |
| | 32 | Present | Female |
| | 33 | Absent | Female |
| | 49 | Absent | Male |

TABLE 2

| Reagent | Amount (μl) |
|---|---|
| 2xmRNA Selective PCR Buffer I | 25 |
| MgCl$_2$ | 10 |
| dNTP/analog mixture | 5 |
| RNase Inhibitor | 1 |
| AMV RTase XL | 1 |
| Oligo dT Primer | 1 |
| RNA | 2 (=2 μg) |
| RNase Free dH$_2$O | 5 |

TABLE 3

| Reagent | Amount to be used (μl) |
|---|---|
| 2xmRNA Selective PCR Buffer I | 20 |
| MgCl$_2$ | 8 |
| dNTP/analog mixture | 4 |
| AMV-Optimized Taq | 1 |
| sense primer | 2.5 |
| antisense primer | 2.5 |
| RT reaction mixture | 10 or 2* |
| dH$_2$O | 2 or 10* |

Example 2

Whether or not the introduced human p300 gene was expressed in various organs of the transgenic mouse was examined by RT-PCR using the primer specific to this gene and RT-Southern hybridization using the probe specific to this gene.

From the heart, lung, liver, kidney of a transgenic mouse (individual no. 6) and the hearts of wild type mice (individual nos. 56, 2, and 59), mRNAs were prepared and RT-PCR was conducted using the mRNAs as templates. The preparation of mRNAs from each organ was conducted in accordance with the manual of RNA extract reagent "ISOGEN" (Nippon Gene Co., Ltd.). RT-PCR was conducted as follows, in accordance with the manual of "mRNA Selective PCR kit" (TaKaRa).

First, the RT reaction mixture having the composition shown in Table 2 was prepared and reacted: for 10 minutes at 30° C.; for 22 minutes at 46° C.; and for 5 minutes at 5° C. Next, a PCR reaction mixture was prepared from various reagents and the above RT reaction mixture having the composition shown in Table 3, and then RT-PCR was conducted under the reaction condition of: 40 cycles (heating and cooling) of 30 seconds at 85° C., 30 seconds at 55° C., and 60 seconds at 72° C. The primers used were as follows.

```
Sense primer:
GCA ACA GGT GCT TAG TAT CC (SEQ ID NO: 5)
(corresponding to 7400 to 7419 bases of p300 gene
(SEQ ID NO: 1))

Antisense primer:
CTG TTG CAT GTG ATG CTG CA (SEQ ID NO: 6)
(corresponding to 7879 to 7898 bases of p300 gene
(SEQ ID NO: 1))
```

The amplified products of RT-PCR were separated by 1% agarose gel electrophoresis and blotted onto nylon filters. Thus RT-Southern hybridization was performed. The hybridization was performed in accordance with the manual of "Express Hyb Hybridization Solution (CLONTECH)". As a probe; a product was used, which was amplified by PCR using pCMVwtp300 as a template and the above primers.

Figure 2:
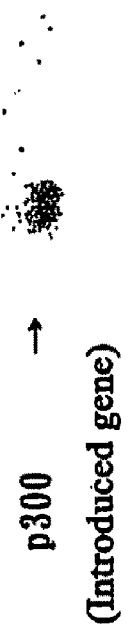
FIG. 2 shows the results of Southern hybridization carried out in Example 2.

The results of RT-Southern hybridization on the transgenic mouse are shown in FIG. 2. As shown in this figure, in the case of the transgenic mouse, p300 genes were expressed only in the heart and not expressed in other organs. And in the case of the wild type mice, p300 genes were not expressed even in the heart thereof. (not shown in the figure).

Example 3

Myocardial cells were taken from transgenic mice (individual nos. 5, 9 and 36) and wild type mice (individual nos. 8, 12 and 35), and proteins were extracted from these cells. Protein extraction was performed in accordance with the method of Hasegawa et al. (Hasegawa K. et al.: Circulation 1997:96:3943-3953). The proteins derived from myocardial cells were examined by Western blotting using anti-human p300 antibodies (CT-Power Clonal™, Upstate Biotechnology Inc.) for confirming whether or not they contain p300. The antibodies are capable of reacting with endogenous mouse p300 not only human-derived p300 that is an expression product of the introduced gene, but also with. The Western blotting was performed in accordance with the method of Morimoto et al. (Morimoto T et al.: The Journal of Biological Chemistry 2000:275:13721-13726).

Figure 3:
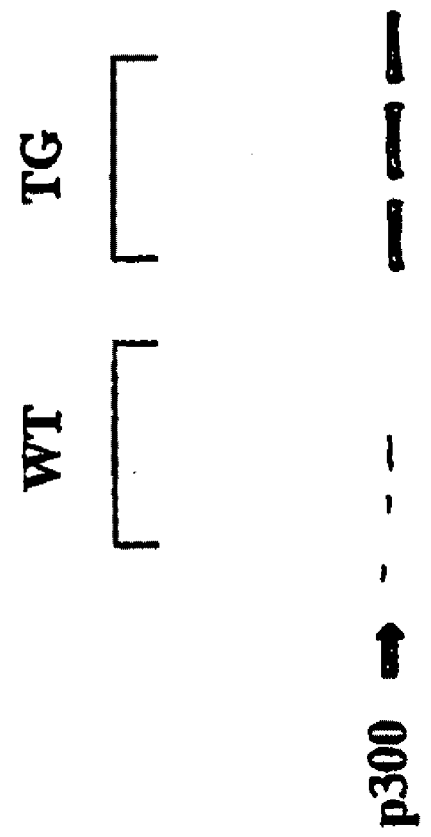
FIG. 3 shows the results of Western blotting carried out in Example 3.
Figure 4A:
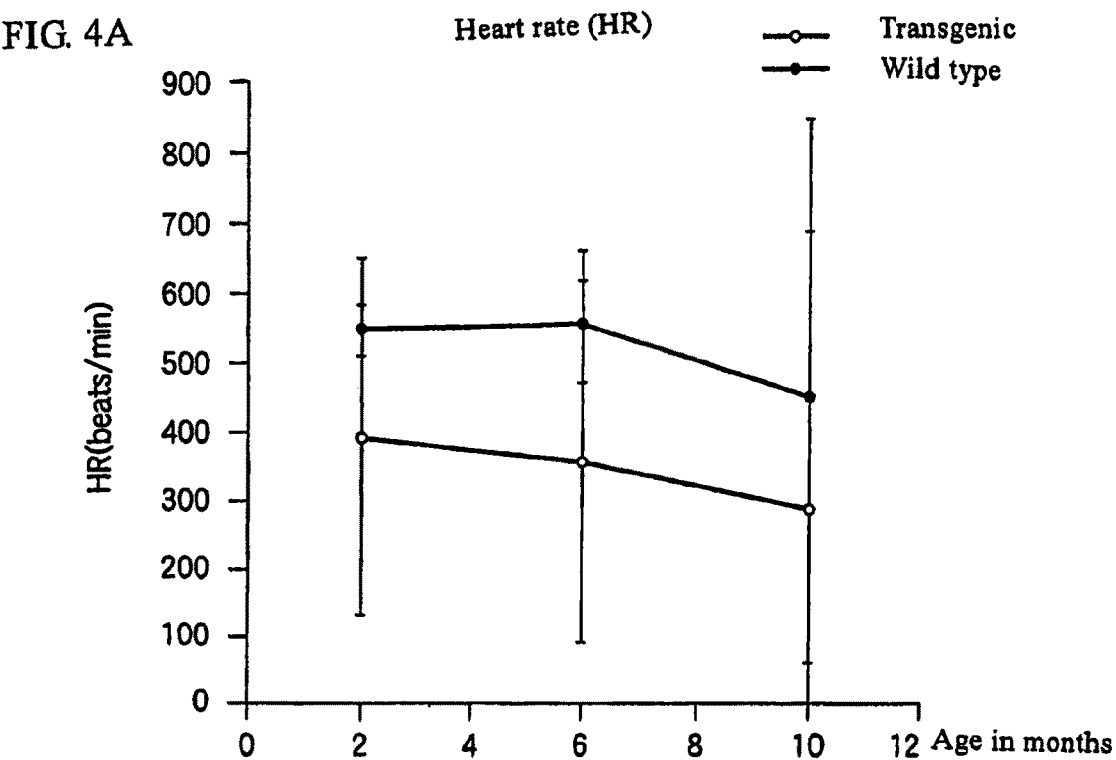
FIG. 4 is a group of graphs (4A to 4F) illustrating comparisons of mice, by ages in months, among measurement values by echocardiography carried out in Example 6.
Figure 4B:
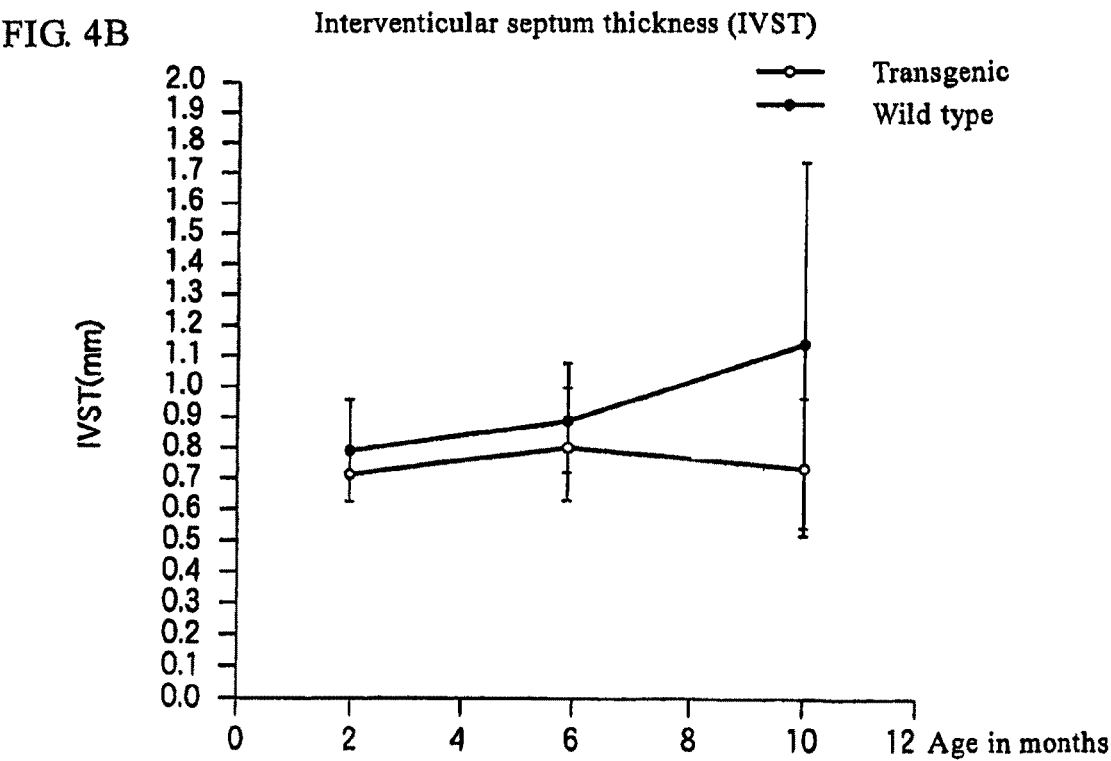
Figure 4C:
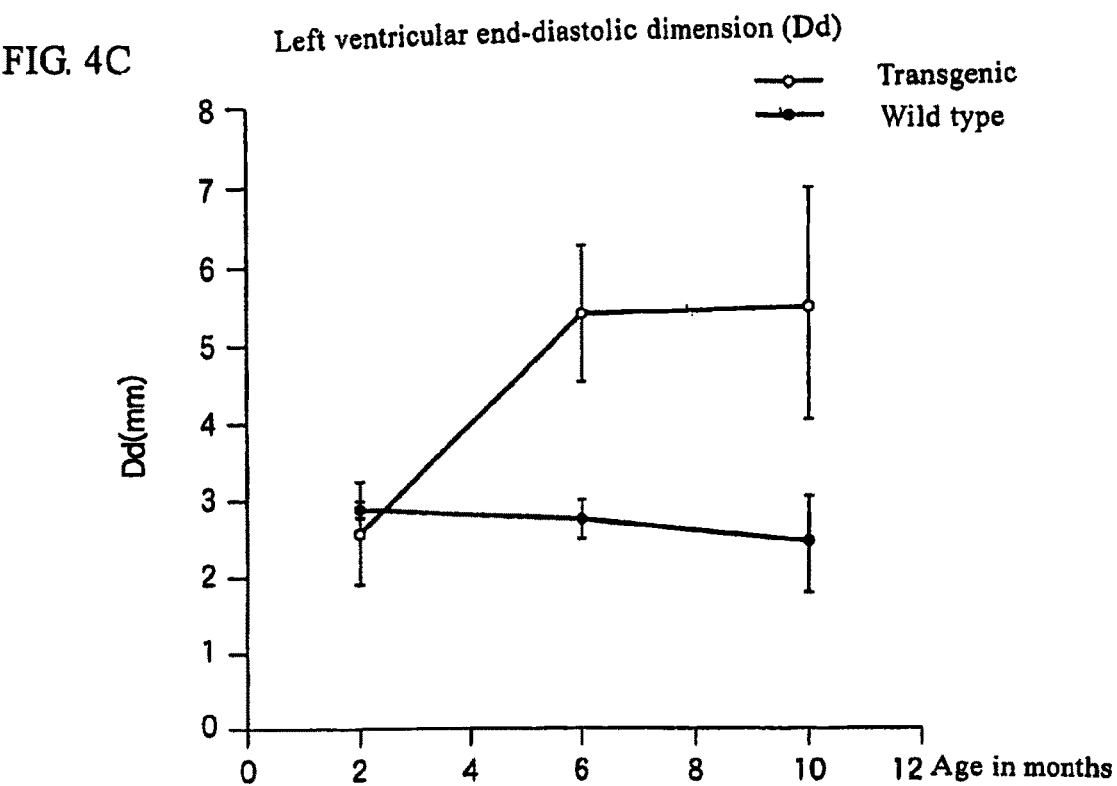
Figure 4D:
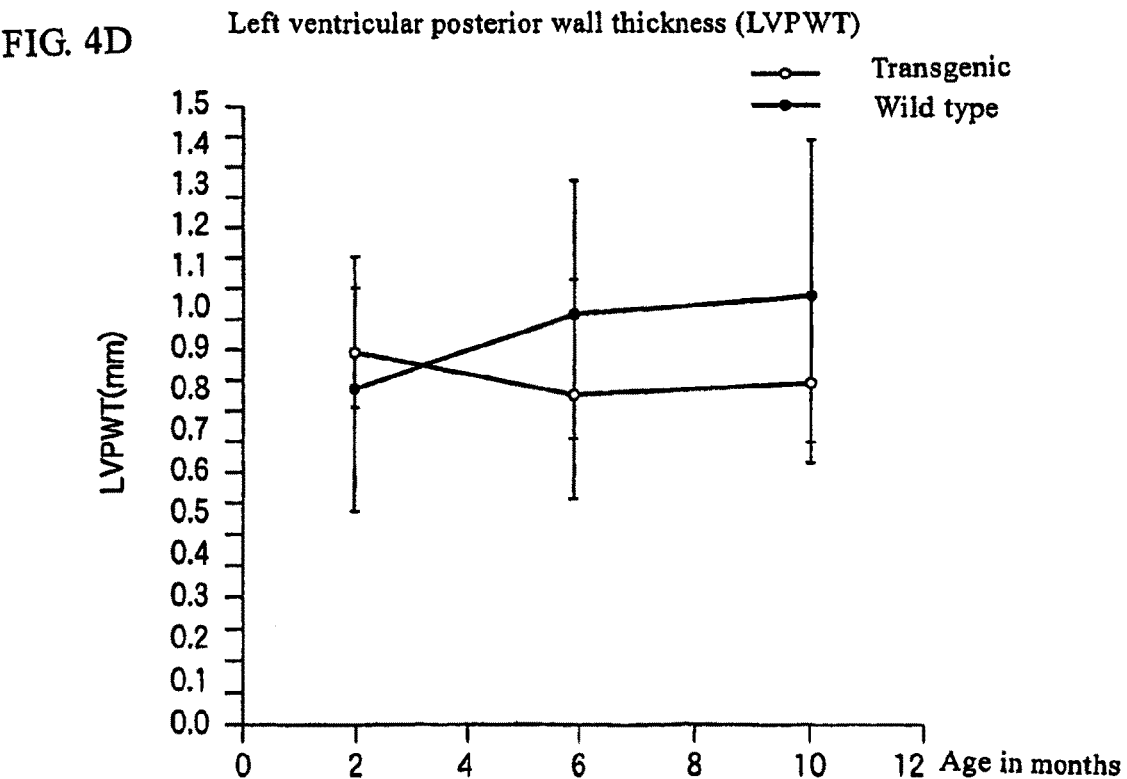
Figure 4E:
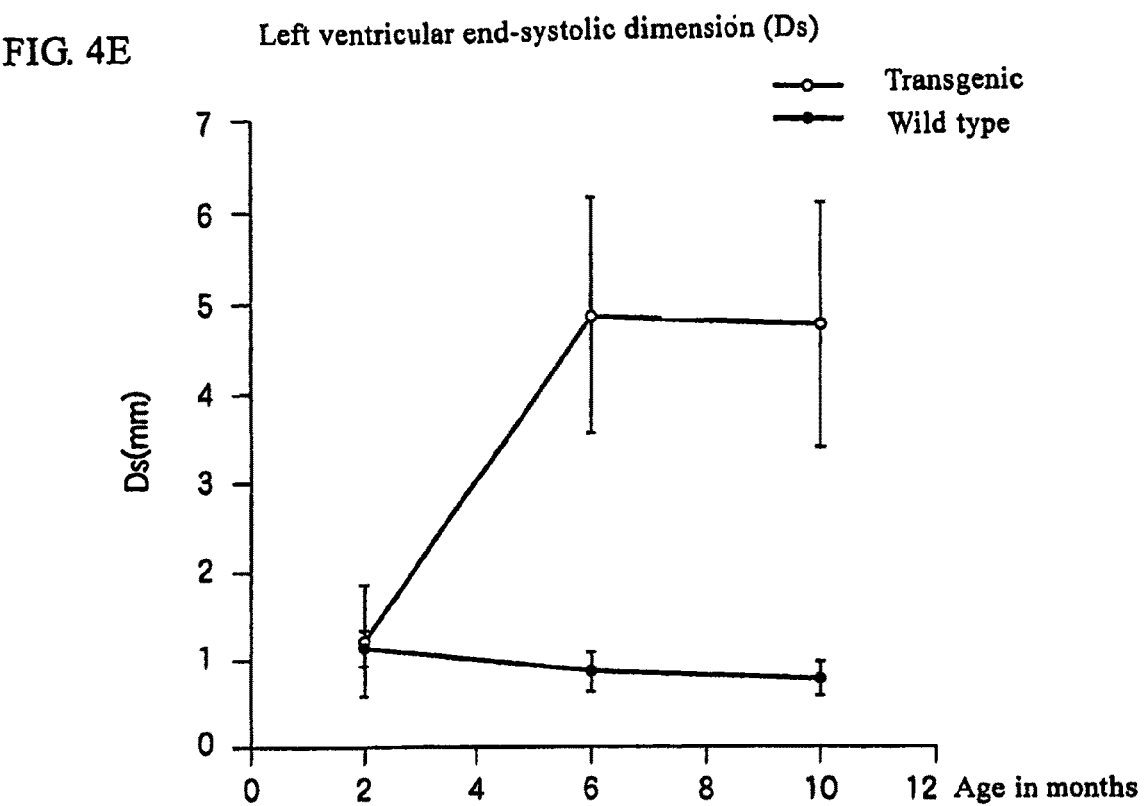
Figure 4F:
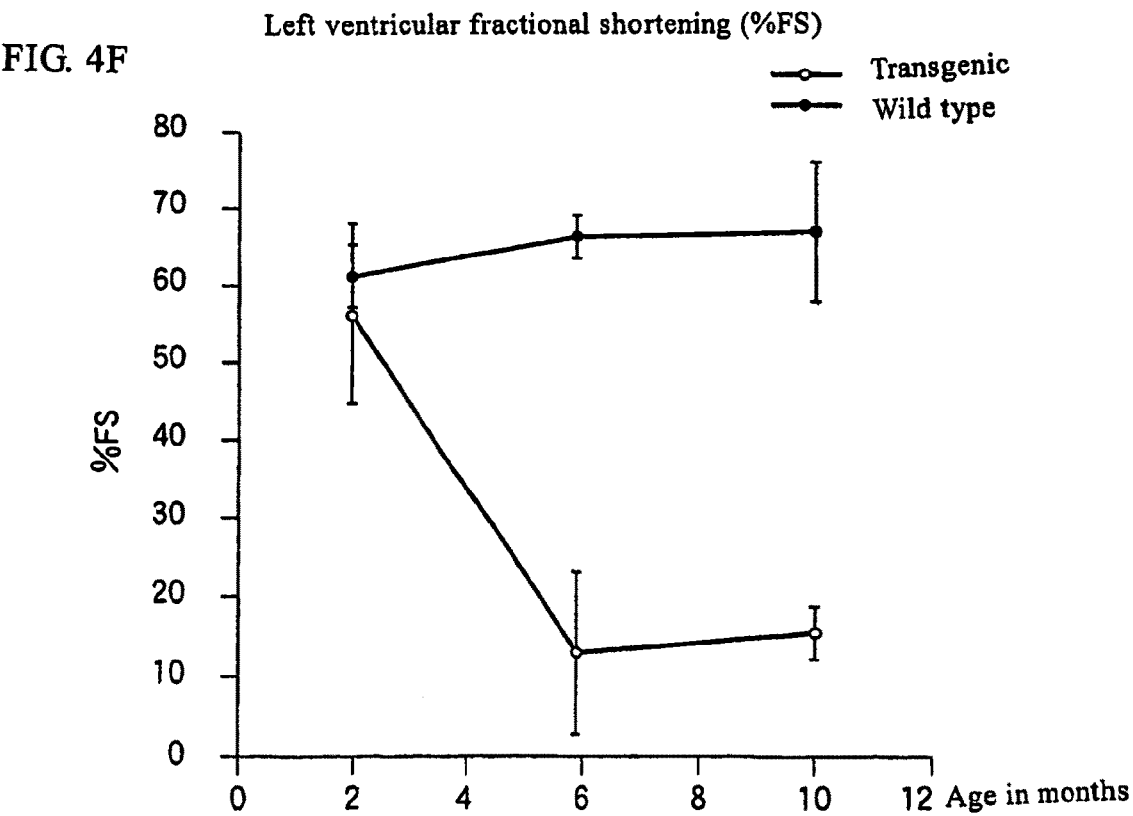

The results of the Western blotting are shown in FIG. 3. As shown in this figure, although p300 was detected from wild type mice (WT), the amount thereof was far less than that of the transgenic mice (TG).

Example 4

The amounts of endothelin-1 in cardiac muscle of mice were determined in accordance with the method of Iwanaga et al. (Circulation 1998 98:2065-2073).

Transgenic mice (individual nos. 1, 3, 7, 20, 32, 34, 51, and 56) and wild type mice (individual nos. 2, 33, 49, 55, and 59) were anesthetized with pentobarbital and the hearts were extirpated. The atria were removed from the heart of each mouse, and the right and left ventricles of the heart were washed with cold physiological saline. The right and left ventricles were put into a Polytron homogenizer with 9 mol/L acetic acid aqueous solution (containing 0.1% Triton-X) and homogenized for 30 seconds, boiled for 7 minutes, and then centrifuged (2000 g, 30 minutes, 4° C.). The supernatant thereof was taken and stored at −80° C.

Extraction of endothelin-1 from the supernatant of the ventricle tissue homogenate was performed in accordance with Kitamura et al. (Kitamura et al. Biochem. Biophys. Res. Commun. 1989; 156:1182-1186). Also, the endothelin-1 content was measured in accordance with the method of Suzuki et al. (Suzuki et al. J. Immunol. Methods. 1989; 118:245-250) using an EIA kit (Wako Pure Chemical Industries, Ltd.). This measurement method enables the detection of endothelin-1 at a concentration of up to 0.5 pg/ml, and further has a crossreactivity of 0.1% or less between endothelin-3 and big endothelin-1.

The endothelin-1 contents in cardiac muscles of individual mice are shown in the following table.

TABLE 4

| Individual No. | Expression type | Endothelin-1 content (pg/ml) |
|---|---|---|
| 2 | Wild type | 3.0 |
| 33 | Wild type | 3.0 |
| 49 | Wild type | 9.0 |
| 55 | Wild type | 7.0 |
| 59 | Wild type | 7.0 |
| 1 | Transgenic | 10.0 |
| 3 | Transgenic | 16.0 |
| 7 | Transgenic | 9.0 |
| 20 | Transgenic | 14.0 |
| 32 | Transgenic | 13.0 |
| 34 | Transgenic | 11.0 |
| 51 | Transgenic | 5.0 |
| 56 | Transgenic | 15.0 |

As shown in the above table, the transgenic mice had noticeably larger amounts of endothelin-1 in the cardiac muscles than the wild type mice.

Example 5

For the purpose of investigating the relationship between the expression of p300 gene and hypertrophy of myocardial cells, heart weights and total body weights of the transgenic mice and wild type mice were examined. The results thereof are shown in the following table.

TABLE 5

| Parent strain | Individual No. | Sex | Expression type | Birth date | Total body weight (kg) | Heart weight (g) | Ratio of heart to total body weight |
|---|---|---|---|---|---|---|---|
| 21 | 4 | Female | Transgenic | 1999 Aug. 17 | 21.1 | 117 | 5.55 |
|  | 5 | Female | Transgenic | 1999 Aug. 17 | 21.2 | 122 | 5.75 |
|  | 6 | Female | Transgenic | 1999 Aug. 17 | 21.4 | 123 | 5.75 |
|  | 25 | Female | Transgenic | 1999 Aug. 17 | 20.9 | 131 | 6.27 |
|  | 11 | Female | Wild type | 1999 Aug. 17 | 23.5 | 120 | 5.11 |
|  | 12 | Female | Wild type | 1999 Aug. 17 | 25 | 102 | 4.08 |
|  | 13 | Female | Wild type | 1999 Aug. 17 | 23.8 | 113 | 4.75 |
|  | 1 | Male | Transgenic | 1999 Aug. 17 | 29.2 | 149 | 5.10 |
|  | 3 | Male | Transgenic | 1999 Aug. 17 | 33 | 155 | 4.70 |
|  | 9 | Male | Transgenic | 1999 Aug. 17 | 29 | 147 | 5.07 |
|  | 2 | Male | Wild type | 1999 Aug. 17 | 30 | 133 | 4.43 |
|  | 7 | Male | Wild type | 1999 Aug. 17 | 27.2 | 137 | 5.04 |
|  | 8 | Male | Wild type | 1999 Aug. 17 | 28.5 | 130 | 4.56 |
| 39 | 20 | Female | Transgenic | 1999 Aug. 18 | 25 | 133 | 5.32 |
|  | 59 | Female | Wild type | 1999 Jun. 28 | 26.7 | 150 | 5.62 |
|  | 56 | Male | Transgenic | 1999 Jun. 28 | 34.1 | 207 | 6.07 |
|  | 55 | Male | Wild type | 1999 Jun. 28 | 31.1 | 145 | 4.66 |
|  | 36 | Male | Transgenic | 1999 Sep. 13 | 27.5 | 146 | 5.31 |
|  | 35 | Male | Wild type | 1999 Sep. 13 | 27.3 | 131 | 4.80 |
| 40 | 34 | Female | Transgenic | 1999 Oct. 1 | 22.9 | 121 | 5.28 |
|  | 32 | Female | Wild type | 1999 Oct. 1 | 21.9 | 112 | 5.11 |
|  | 33 | Female | Wild type | 1999 Oct. 1 | 22.3 | 110 | 4.93 |
|  | 50 | Male | Transgenic | 1999 Oct. 20 | 24.7 | 125 | 5.06 |
|  | 51 | Male | Transgenic | 1999 Oct. 20 | 26 | 125 | 4.81 |
|  | 48 | Male | Wild type | 1999 Oct. 20 | 23.9 | 104 | 4.35 |
|  | 49 | Male | Wild type | 1999 Oct. 20 | 26.3 | 148 | 5.63 |

Among the individuals indicated in the above table, groups were made of individuals having the same parent strain, sex, and birth date. The expression type and the ratio of heart to total body weight were investigated within such groups. The results thereof were shown in the table below.

TABLE 6

| Group | Expression type | Individual No. | Average ratio of heart to total body weight |
|---|---|---|---|
| A | Transgenic | 4, 5, 6, 25 | 5.83 |
|  | Wild type | 11, 12, 13 | 4.64 |
| B | Transgenic | 1, 3, 9 | 4.96 |
|  | Wild type | 2, 7, 8, | 4.68 |
| C | Transgenic | 56 | 6.07 |
|  | Wild type | 55 | 4.66 |
| D | Transgenic | 36 | 5.31 |
|  | Wild type | 35 | 4.80 |

As shown in the above table, the heart to total body weight ratios of the transgenic mice were approximately 10 to 30% higher than those of the wild type mice.

Example 6

For the purpose of investigating the relationship between the expression of p300 gene and hypertrophy of myocardial cells, echocardiography was performed on transgenic and wild type mice with ages of 2, 6 and 10 months.

The mice were anesthetized with ketamine (50 mg/kg) and xylazine (2.5 mg/kg), and transthoracic echocardiography was performed with a cardiac ultrasound recorder (Toshiba Power Vision SSA-380A), using a 7.5-MHz transducer.

After obtaining high quality two-dimensional images, echocardiography were performed in M mode, and left ventricular end-diastolic dimension (LVDd) and left ventricular end-systolic dimension (LVDs) were measured by the leading-edge-to-leading-edge convention adopted by the American Society of Echocardiography. Further, left ventricular fractional shortening (% FS) was calculated in accordance with the equation below.

$$\% FS = [(LVDd - LVDs)/LVDd] \times 100$$

In addition, the other measured values were treated by referring to the method of Inoko et al. (Inoko et al. Am. J. Physiol. 1994; 267:2471-2481).

The results are shown in the following table and in FIGS. 4 and 5. The notations used in the table and figures are as follows.

HR: Heart rate (beat/min)
(LV)Dd: Left ventricular end-diastolic dimension (unit: mm)
(LV)Ds: Left ventricular end-systolic dimension (unit: mm)
IVST: Interventricular septum thickness (unit: mm)
LVPWT: Left ventricular posterior wall thickness (unit: mm)
% FS: Left ventricular fractional shortening As understood from the above table and FIGS. 4 and 5, with respect to left ventricular end-diastolic and left ventricular end-systolic dimensions, there was almost no difference at the age of 2 months. However, at the ages of 6 months and 10 months, the transgenic mice showed significantly larger values on these dimensions than the wild type mice. Further, at the ages of 6 months and 10 months, the transgenic mice had lower heart rates and left ventricular fractional shortenings, and thus it was recognized that the transgenic mice suffered from heart failures. In addition, there were small changes according to age in interventricular septum thickness and left ventricular posterior wall thickness, and no statistical significances thereon were observed between the transgenic mice and wild type mice.

All publications, patents and patent applications cited herein are incorporated by reference in their entirety.

INDUSTRIAL APPLICABILITY

The present invention provides a novel transgenic animal. This transgenic animal is useful for elucidation of the onset mechanism of heart failure and development of therapeutic agents for heart failure.

Sequence Listing Free Text

SEQ ID NO:3: A sense primer used for PCR in Example 1
SEQ ID NO: 4: An antisense primer used for PCR in Example 1
SEQ ID NO: 5: A sense primer used for PCR in Example 2
SEQ ID NO: 6: An antisense primer used for PCR in Example 2

TABLE 7

| Parent strain | ID No. | Expression type | Sex | Age in months | HR | Dd | Ds | IVST | LVPWT | % FS |
|---|---|---|---|---|---|---|---|---|---|---|
| 39 | 334 | Transgenic | F | 2 | 570 | 2.2 | 0.6 | 0.8 | 1.1 | 72.7 |
|  | 335 | Transgenic | F | 2 | 517 | 2.1 | 0.9 | 0.6 | 0.8 | 57.1 |
|  | 336 | Wild type | F | 2 |  |  |  |  |  |  |
|  | 337 | Wild type | F | 2 |  |  |  |  |  |  |
|  | 338 | Wild type | F | 2 |  |  |  |  |  |  |
| 39 | 339 | Wild type | M | 2 | 556 | 3 | 1.3 | 0.9 | 0.7 | 56.7 |
|  | 340 | Transgenic | M | 2 | 500 | 3.7 | 2.1 | 0.7 | 0.8 | 43.2 |
|  | 341 | Wild type | M | 2 | 517 | 2.9 | 1 | 0.6 | 0.6 | 65.5 |
|  | 342 | Transgenic | M | 2 |  | 2.9 | 1.3 | 0.8 | 1 | 55.2 |
|  | 343 | Wild type | M | 2 | 584 | 3.1 | 1.1 | 0.9 | 1.2 | 64.5 |
| 39 | 280 | Transgenic | F | 6 | 600 | 4.7 | 3.9 | 0.8 | 0.7 | 17.0 |
|  | 281 | Transgenic | F | 6 | 652 | 4.6 | 3.3 | 1 | 0.8 | 28.3 |
|  | 284 | Wild type | F | 6 | 450 | 3.1 | 1 | 1.1 | 0.8 | 67.7 |
|  | 285 | Wild type | F | 6 | 506 | 2.5 | 0.7 | 0.8 | 1.5 | 72.0 |
| 39 | 286 | Transgenic | M | 6 | 300 | 6.2 | 6 | 0.7 | 0.6 | 3.2 |
|  | 287 | Wild type | M | 6 | 616 | 3 | 1 | 0.7 | 0.9 | 66.7 |
|  | 288 | Wild type | M | 6 | 682 | 2.8 | 1 | 1 | 0.9 | 64.3 |
|  | 289 | Transgenic | M | 6 | 250 | 6.7 | 6.4 | 1 | 0.7 | 4.5 |
|  | 290 | Transgenic | M | 6 |  | 6 | 5.2 | 0.6 | 1.3 | 13.3 |
| 40 | 203 | Transgenic | M | 10 | 584 | 4.7 | 3.8 | 0.9 | 1 | 19.1 |
|  | 206 | Wild type | M | 10 |  | 2.1 | 0.7 | 1.8 | 1.5 | 66.7 |
|  | 207 | Transgenic | M | 10 |  | 6.8 | 5.8 | 0.6 | 0.7 | 14.7 |
|  | 227 | Transgenic | M | 10 |  |  |  |  |  |  |
|  | 228 | Wild type | M | 10 | 692 | 3.3 | 0.7 | 0.6 | 0.8 | 78.8 |
|  | 229 | Wild type | M | 10 | 682 | 2.3 | 0.9 | 1 | 0.9 | 60.9 |
|  | 230 | Transgenic | M | 10 |  |  |  |  |  |  |

Blank: N.D.

The invention claimed is:

1. A transgenic mouse which exhibits cardiac hypertrophy, whose genome comprises a gene comprising nucleic acid sequence from 1200 to 8441 of SEQ ID NO:1, which is operably linked to α-myosin heavy chain promoter exerting its activity in myocardial cells.

2. The transgenic mouse according to claim 1, wherein the mouse has at least one phenotype selected from the group consisting of a larger amount of endothelin-1 in the cardiac muscles than that of a wild type mouse, and a higher heart to total body weight ratio than that of a wild type mouse.

3. A method of screening a substance having therapeutic activity for heart failure, the method comprising the steps of:
   (1) administering a test substance to the transgenic mouse according to claim 2;
   (2) confirming whether or not cardiac hypertrophy is suppressed in the transgenic mouse; and
   (3) selecting the test substance as the substance having therapeutic activity for heart failure when cardiac hypertrophy is suppressed in the transgenic mouse.

4. A method of screening a substance having therapeutic activity for heart failure, the method comprising the steps of:
   (1) administering a test substance to the transgenic mouse according to claim 1;
   (2) confirming whether or not cardiac hypertrophy is suppressed in the transgenic mouse; and
   (3) selecting the test substance as the substance having therapeutic activity for heart failure when cardiac hypertrophy is suppressed in the transgenic mouse.

* * * * *

SEQUENCE LISTING

<160> NUMBER OF SEQ ID NOS: 6

<210> SEQ ID NO 1
<211> LENGTH: 9046
<212> TYPE: DNA
<213> ORGANISM: Homo sapiens
<220> FEATURE:
<221> NAME/KEY: CDS
<222> LOCATION: (1200)..(8441)

<400> SEQUENCE: 1

```
ccttgtttgt gtgctaggct gggggggaga gagggcgaga gagagcgggc gagagtgggc        60
aagcaggacg ccgggctgag tgctaactgc gggacgcaga gagtgcggag gggagtcggg       120
tcggagagag gcgcagggg ccagaacagt ggcaggggc ccggggcgca cgggctgagg        180
cgacccccag cccctcccg tccgcacaca ccccaccgc ggtccagcag ccgggccggc        240
gtcgacgcta gggggacca ttacataacc cgcgccccgg ccgtcttctc ccgccgccgc       300
ggcgcccgaa ctgagcccgg ggcgggcgct ccagcactgg ccgccggcgt ggggcgtagc      360
agcggccgta ttattattc gcggaaagga aggcgaagga ggggagcgcc ggcgcgagga       420
ggggccgcct gcgcccgccg ccggagcggg gcctcctcgg tgggctccgc gtcggcgcgg      480
gcgtgcgggc ggcgctgctc ggccggcc cctcggccct ctggtccggc cagctccgct        540
cccggcgtcc ttgccgcgcc tccgccggcc gccgcgcgat gtgaggcggc ggcgccagcc      600
tggctctcgg ctcgggcgag ttctctgcgg ccattagggg ccggtgcggc ggcggcgcgg      660
agcgcggcgg caggaggagg gttcggaggg tgggggcgca ggcccgggag ggggcaccgg      720
gaggaggtga gtgtctcttg tcgcctcctc ctctccccc ttttcgcccc cgcctccttg       780
tggcgatgag aaggaggagg acagcgccga ggaggaagag gttgatggcg gcggcggagc      840
tccgagagac ctcggctggg caggggccgg ccgtggcggg ccggggactg cgcctctaga      900
gccgcgagtt ctcgggaatt cgccgcagcg accggcctc ggcgaatttg tgctcttgtg       960
ccctcctccg ggcttgggcc aggccggcc ctcgcacttg cccttacctt ttctatcgag      1020
tccgcatccc tctccagcca ctgcgacccg gcgaagagaa aaaggaactt ccccaccccc     1080
ctcgggtgcc gtcggagccc cccagcccac ccctgggtgc ggcgcgggga ccccgggccg    1140
aagaagagat ttcctgagga ttctggtttt cctcgcttgt atctccgaaa gaattaaaa    1199
```

| | | | | | | | | | | | | | | | | |
|---|---|---|---|---|---|---|---|---|---|---|---|---|---|---|---|---|
|atg|gcc|gag|aat|gtg|gtg|gaa|ccg|ggg|ccg|cct|tca|gcc|aag|cgg|cct|1247|
|Met|Ala|Glu|Asn|Val|Val|Glu|Pro|Gly|Pro|Pro|Ser|Ala|Lys|Arg|Pro|
|1| | | |5| | | | |10| | | | |15| | |

| | | | | | | | | | | | | | | | | |
|---|---|---|---|---|---|---|---|---|---|---|---|---|---|---|---|---|
|aaa|ctc|tca|tct|ccg|gcc|ctc|tcg|gcg|tcc|gcc|agc|gat|ggc|aca|gat|1295|
|Lys|Leu|Ser|Ser|Pro|Ala|Leu|Ser|Ala|Ser|Ala|Ser|Asp|Gly|Thr|Asp|
| | | | |20| | | | |25| | | | |30| | |

| | | | | | | | | | | | | | | | | |
|---|---|---|---|---|---|---|---|---|---|---|---|---|---|---|---|---|
|ttt|ggc|tct|cta|ttt|gac|ttg|gag|cac|gac|tta|cca|gat|gaa|tta|atc|1343|
|Phe|Gly|Ser|Leu|Phe|Asp|Leu|Glu|His|Asp|Leu|Pro|Asp|Glu|Leu|Ile|
| | | |35| | | | |40| | | | |45| | | |

| | | | | | | | | | | | | | | | | |
|---|---|---|---|---|---|---|---|---|---|---|---|---|---|---|---|---|
|aac|tct|aca|gaa|ttg|gga|cta|acc|aat|ggt|ggt|gat|att|aat|cag|ctt|1391|
|Asn|Ser|Thr|Glu|Leu|Gly|Leu|Thr|Asn|Gly|Gly|Asp|Ile|Asn|Gln|Leu|
| | |50| | | | |55| | | | |60| | | | |

| | | | | | | | | | | | | | | | | |
|---|---|---|---|---|---|---|---|---|---|---|---|---|---|---|---|---|
|cag|aca|agt|ctt|ggc|atg|gta|caa|gat|gca|gct|tct|aaa|cat|aaa|cag|1439|
|Gln|Thr|Ser|Leu|Gly|Met|Val|Gln|Asp|Ala|Ala|Ser|Lys|His|Lys|Gln|
|65| | | | |70| | | | |75| | | | |80| |

| | | | | | | | | | | | | | | | | |
|---|---|---|---|---|---|---|---|---|---|---|---|---|---|---|---|---|
|ctg|tca|gaa|ttg|ctg|cga|tct|ggt|agt|tcc|cct|aac|ctc|aat|atg|gga|1487|
|Leu|Ser|Glu|Leu|Leu|Arg|Ser|Gly|Ser|Ser|Pro|Asn|Leu|Asn|Met|Gly|
| | | | |85| | | | |90| | | | |95| | |

| | | | | | | | | | | | | | | | | |
|---|---|---|---|---|---|---|---|---|---|---|---|---|---|---|---|---|
|gtt|ggt|ggc|cca|ggt|caa|gtc|atg|gcc|agc|cag|gcc|caa|cag|agc|agt|1535|

-continued

|  |  |  |
|---|---|---|
| Val Gly Gly Pro Gly Gln Val Met Ala Ser Gln Ala Gln Ser Ser<br>100          105            110 | | |
| cct gga tta ggt ttg ata aat agc atg gtc aaa agc cca atg aca cag<br>Pro Gly Leu Gly Leu Ile Asn Ser Met Val Lys Ser Pro Met Thr Gln<br>115          120            125 | | 1583 |
| gca ggc ttg act tct ccc aac atg ggg atg ggc act agt gga cca aat<br>Ala Gly Leu Thr Ser Pro Asn Met Gly Met Gly Thr Ser Gly Pro Asn<br>130          135            140 | | 1631 |
| cag ggt cct acg cag tca aca ggt atg atg aac agt cca gta aat cag<br>Gln Gly Pro Thr Gln Ser Thr Gly Met Met Asn Ser Pro Val Asn Gln<br>145          150            155          160 | | 1679 |
| cct gcc atg gga atg aac aca ggg acg aat gcg ggc atg aat cct gga<br>Pro Ala Met Gly Met Asn Thr Gly Thr Asn Ala Gly Met Asn Pro Gly<br>165            170            175 | | 1727 |
| atg ttg gct gca ggc aat gga caa ggg ata atg cct aat caa gtc atg<br>Met Leu Ala Ala Gly Asn Gly Gln Gly Ile Met Pro Asn Gln Val Met<br>180            185            190 | | 1775 |
| aac ggt tca att gga gca ggc cga ggg cga cag gat atg cag tac cca<br>Asn Gly Ser Ile Gly Ala Gly Arg Gly Arg Gln Asp Met Gln Tyr Pro<br>195            200            205 | | 1823 |
| aac cca ggc atg gga agt gct ggc aac tta ctg act gag cct ctt cag<br>Asn Pro Gly Met Gly Ser Ala Gly Asn Leu Leu Thr Glu Pro Leu Gln<br>210            215            220 | | 1871 |
| cag ggc tct ccc cag atg gga gga caa aca gga ttg aga ggc ccc cag<br>Gln Gly Ser Pro Gln Met Gly Gly Gln Thr Gly Leu Arg Gly Pro Gln<br>225          230            235          240 | | 1919 |
| cct ctt aag atg gga atg atg aac aac ccc aat cct tat ggt tca cca<br>Pro Leu Lys Met Gly Met Met Asn Asn Pro Asn Pro Tyr Gly Ser Pro<br>245            250            255 | | 1967 |
| tat act cag aat cct gga cag cag att gga gcc agt ggc ctt ggt ctc<br>Tyr Thr Gln Asn Pro Gly Gln Gln Ile Gly Ala Ser Gly Leu Gly Leu<br>260            265            270 | | 2015 |
| cag att cag aca aaa act gta cta tca aat aac tta tct cca ttt gct<br>Gln Ile Gln Thr Lys Thr Val Leu Ser Asn Asn Leu Ser Pro Phe Ala<br>275            280            285 | | 2063 |
| atg gac aaa aag gca gtt cct ggt gga gga atg ccc aac atg ggt caa<br>Met Asp Lys Lys Ala Val Pro Gly Gly Gly Met Pro Asn Met Gly Gln<br>290            295            300 | | 2111 |
| cag cca gcc ccg cag gtc cag cag cca ggt ctg gtg act cca gtt gcc<br>Gln Pro Ala Pro Gln Val Gln Gln Pro Gly Leu Val Thr Pro Val Ala<br>305          310            315          320 | | 2159 |
| caa ggg atg ggt tct gga gca cat aca gct gat cca gag aag cgc aag<br>Gln Gly Met Gly Ser Gly Ala His Thr Ala Asp Pro Glu Lys Arg Lys<br>325            330            335 | | 2207 |
| ctc atc cag cag cag ctt gtt ctc ctt ttg cat gct cac aag tgc cag<br>Leu Ile Gln Gln Gln Leu Val Leu Leu Leu His Ala His Lys Cys Gln<br>340            345            350 | | 2255 |
| cgc cgg gaa cag gcc aat ggg gaa gtg agg cag tgc aac ctt ccc cac<br>Arg Arg Glu Gln Ala Asn Gly Glu Val Arg Gln Cys Asn Leu Pro His<br>355            360            365 | | 2303 |
| tgt cgc aca atg aag aat gtc cta aac cac atg aca cac tgc cag tca<br>Cys Arg Thr Met Lys Asn Val Leu Asn His Met Thr His Cys Gln Ser<br>370            375            380 | | 2351 |
| ggc aag tct tgc caa gtg gca cac tgt gca tct tct cga caa atc att<br>Gly Lys Ser Cys Gln Val Ala His Cys Ala Ser Ser Arg Gln Ile Ile<br>385            390            395          400 | | 2399 |
| tca cac tgg aag aat tgt aca aga cat gat tgt cct gtg tgt ctc ccc<br>Ser His Trp Lys Asn Cys Thr Arg His Asp Cys Pro Val Cys Leu Pro<br>405            410            415 | | 2447 |
| ctc aaa aat gct ggt gat aag aga aat caa cag cca att ttg act gga | | 2495 |

-continued

| | | |
|---|---|---|
| Leu Lys Asn Ala Gly Asp Lys Arg Asn Gln Gln Pro Ile Leu Thr Gly<br>420 425 430 | | |
| gca ccc gtt gga ctt gga aat cct agc tct cta ggg gtg ggt caa cag<br>Ala Pro Val Gly Leu Gly Asn Pro Ser Ser Leu Gly Val Gly Gln Gln<br>435 440 445 | | 2543 |
| tct gcc ccc aac cta agc act gtt agt cag att gat ccc agc tcc ata<br>Ser Ala Pro Asn Leu Ser Thr Val Ser Gln Ile Asp Pro Ser Ser Ile<br>450 455 460 | | 2591 |
| gaa aga gcc tat gca gct ctt gga cta ccc tat caa gta aat cag atg<br>Glu Arg Ala Tyr Ala Ala Leu Gly Leu Pro Tyr Gln Val Asn Gln Met<br>465 470 475 480 | | 2639 |
| ccg aca caa ccc cag gtg caa gca aag aac cag cag aat cag cag cct<br>Pro Thr Gln Pro Gln Val Gln Ala Lys Asn Gln Gln Asn Gln Gln Pro<br>485 490 495 | | 2687 |
| ggg cag tct ccc caa ggc atg cgg ccc atg agc aac atg agt gct agt<br>Gly Gln Ser Pro Gln Gly Met Arg Pro Met Ser Asn Met Ser Ala Ser<br>500 505 510 | | 2735 |
| cct atg gga gta aat gga ggt gta gga gtt caa acg ccg agt ctt ctt<br>Pro Met Gly Val Asn Gly Gly Val Gly Val Gln Thr Pro Ser Leu Leu<br>515 520 525 | | 2783 |
| tct gac tca atg ttg cat tca gcc ata aat tct caa aac cca atg atg<br>Ser Asp Ser Met Leu His Ser Ala Ile Asn Ser Gln Asn Pro Met Met<br>530 535 540 | | 2831 |
| agt gaa aat gcc agt gtg ccc tcc ctg ggt cct atg cca aca gca gct<br>Ser Glu Asn Ala Ser Val Pro Ser Leu Gly Pro Met Pro Thr Ala Ala<br>545 550 555 560 | | 2879 |
| caa cca tcc act act gga att cgg aaa cag tgg cac gaa gat att act<br>Gln Pro Ser Thr Thr Gly Ile Arg Lys Gln Trp His Glu Asp Ile Thr<br>565 570 575 | | 2927 |
| cag gat ctt cga aat cat ctt gtt cac aaa ctc gtc caa gcc ata ttt<br>Gln Asp Leu Arg Asn His Leu Val His Lys Leu Val Gln Ala Ile Phe<br>580 585 590 | | 2975 |
| cct acg ccg gat cct gct gct tta aaa gac aga cgg atg gaa aac cta<br>Pro Thr Pro Asp Pro Ala Ala Leu Lys Asp Arg Arg Met Glu Asn Leu<br>595 600 605 | | 3023 |
| gtt gca tat gct cgg aaa gtt gaa ggg gac atg tat gaa tct gca aac<br>Val Ala Tyr Ala Arg Lys Val Glu Gly Asp Met Tyr Glu Ser Ala Asn<br>610 615 620 | | 3071 |
| aat cga gcg gaa tac tac cac ctt cta gct gag aaa atc tat aag atc<br>Asn Arg Ala Glu Tyr Tyr His Leu Leu Ala Glu Lys Ile Tyr Lys Ile<br>625 630 635 640 | | 3119 |
| cag aaa gaa cta gaa gaa aaa cga agg acc aga cta cag aag cag aac<br>Gln Lys Glu Leu Glu Glu Lys Arg Arg Thr Arg Leu Gln Lys Gln Asn<br>645 650 655 | | 3167 |
| atg cta cca aat gct gca ggc atg gtt cca gtt tcc atg aat cca ggg<br>Met Leu Pro Asn Ala Ala Gly Met Val Pro Val Ser Met Asn Pro Gly<br>660 665 670 | | 3215 |
| cct aac atg gga cag ccg caa cca gga atg act tct aat ggc cct cta<br>Pro Asn Met Gly Gln Pro Gln Pro Gly Met Thr Ser Asn Gly Pro Leu<br>675 680 685 | | 3263 |
| cct gac cca agt atg atc cgt ggc agt gtg cca aac cag atg atg cct<br>Pro Asp Pro Ser Met Ile Arg Gly Ser Val Pro Asn Gln Met Met Pro<br>690 695 700 | | 3311 |
| cga ata act cca caa tct ggt ttg aat caa ttt ggc cag atg agc atg<br>Arg Ile Thr Pro Gln Ser Gly Leu Asn Gln Phe Gly Gln Met Ser Met<br>705 710 715 720 | | 3359 |
| gcc cag ccc cct att gta ccc cgg caa acc cct cct ctt cag cac cat<br>Ala Gln Pro Pro Ile Val Pro Arg Gln Thr Pro Pro Leu Gln His His<br>725 730 735 | | 3407 |
| gga cag ttg gct caa cct gga gct ctc aac ccg cct atg ggc tat ggg | | 3455 |

|  |  |
|---|---|
| Gly Gln Leu Ala Gln Pro Gly Ala Leu Asn Pro Pro Met Gly Tyr Gly<br>                740                 745                 750 | |
| cct cgt atg caa cag cct tcc aac cag ggc cag ttc ctt cct cag act<br>Pro Arg Met Gln Gln Pro Ser Asn Gln Gly Gln Phe Leu Pro Gln Thr<br>        755                 760                 765 | 3503 |
| cag ttc cca tca cag gga atg aat gta aca aat atc cct ttg gct ccg<br>Gln Phe Pro Ser Gln Gly Met Asn Val Thr Asn Ile Pro Leu Ala Pro<br>770                 775                 780 | 3551 |
| tcc agc ggt caa gct cca gtg tct caa gca caa atg tct agt tct tcc<br>Ser Ser Gly Gln Ala Pro Val Ser Gln Ala Gln Met Ser Ser Ser Ser<br>785                 790                 795                 800 | 3599 |
| tgc ccg gtg aac tct cct ata atg cct cca ggg tct cag ggg agc cac<br>Cys Pro Val Asn Ser Pro Ile Met Pro Pro Gly Ser Gln Gly Ser His<br>            805                 810                 815 | 3647 |
| att cac tgt ccc cag ctt cct caa cca gct ctt cat cag aat tca ccc<br>Ile His Cys Pro Gln Leu Pro Gln Pro Ala Leu His Gln Asn Ser Pro<br>            820                 825                 830 | 3695 |
| tcg cct gta cct agt cgt acc ccc acc cct cac cat act ccc cca agc<br>Ser Pro Val Pro Ser Arg Thr Pro Thr Pro His His Thr Pro Pro Ser<br>            835                 840                 845 | 3743 |
| ata ggg gct cag cag cca cca gca aca aca att cca gcc cct gtt cct<br>Ile Gly Ala Gln Gln Pro Pro Ala Thr Thr Ile Pro Ala Pro Val Pro<br>850                 855                 860 | 3791 |
| aca cca cca gcc atg cca cct ggg cca cag tcc cag gct cta cat ccc<br>Thr Pro Pro Ala Met Pro Pro Gly Pro Gln Ser Gln Ala Leu His Pro<br>865                 870                 875                 880 | 3839 |
| cct cca agg cag aca cct aca cca cca aca aca caa ctt ccc caa caa<br>Pro Pro Arg Gln Thr Pro Thr Pro Pro Thr Thr Gln Leu Pro Gln Gln<br>            885                 890                 895 | 3887 |
| gtg cag cct tca ctt cct gct gca cct tct gct gac cag ccc cag cag<br>Val Gln Pro Ser Leu Pro Ala Ala Pro Ser Ala Asp Gln Pro Gln Gln<br>            900                 905                 910 | 3935 |
| cag cct cgc tca cag cag agc aca gca gcg tct gtt cct acc cca aac<br>Gln Pro Arg Ser Gln Gln Ser Thr Ala Ala Ser Val Pro Thr Pro Asn<br>            915                 920                 925 | 3983 |
| gca ccg ctg ctt cct ccg cag cct gca act cca ctt tcc cag cca gct<br>Ala Pro Leu Leu Pro Pro Gln Pro Ala Thr Pro Leu Ser Gln Pro Ala<br>930                 935                 940 | 4031 |
| gta agc att gaa gga cag gta tca aat cct cca tct act agt agc aca<br>Val Ser Ile Glu Gly Gln Val Ser Asn Pro Pro Ser Thr Ser Ser Thr<br>945                 950                 955                 960 | 4079 |
| gaa gtg aat tct cag gcc att gct gag aag cag cct tcc cag gaa gtg<br>Glu Val Asn Ser Gln Ala Ile Ala Glu Lys Gln Pro Ser Gln Glu Val<br>            965                 970                 975 | 4127 |
| aag atg gag gcc aaa atg gaa gtg gat caa cca gaa cca gca gat acg<br>Lys Met Glu Ala Lys Met Glu Val Asp Gln Pro Glu Pro Ala Asp Thr<br>            980                 985                 990 | 4175 |
| cag ccg gag gat att tca gag tct aaa gtg gaa gac tgt aaa atg gaa<br>Gln Pro Glu Asp Ile Ser Glu Ser Lys Val Glu Asp Cys Lys Met Glu<br>            995                 1000                1005 | 4223 |
| tct acc gaa aca gaa gag aga agc act gag tta aaa act gaa ata aaa<br>Ser Thr Glu Thr Glu Glu Arg Ser Thr Glu Leu Lys Thr Glu Ile Lys<br>        1010                1015                1020 | 4271 |
| gag gag gaa gac cag cca agt act tca gct acc cag tca tct ccg gct<br>Glu Glu Glu Asp Gln Pro Ser Thr Ser Ala Thr Gln Ser Ser Pro Ala<br>1025                1030                1035                1040 | 4319 |
| cca gga cag tca aag aaa aag att ttc aaa cca gaa gaa cta cga cag<br>Pro Gly Gln Ser Lys Lys Lys Ile Phe Lys Pro Glu Glu Leu Arg Gln<br>                1045                1050                1055 | 4367 |
| gca ctg atg cca aca ttg gag gca ctt tac cgt cag gat cca gaa tcc | 4415 |

```
Ala Leu Met Pro Thr Leu Glu Ala Leu Tyr Arg Gln Asp Pro Glu Ser
        1060                1065                1070 ctt ccc ttt cgt caa cct gtg gac cct cag ctt tta gga atc cct gat    4463
Leu Pro Phe Arg Gln Pro Val Asp Pro Gln Leu Leu Gly Ile Pro Asp
    1075                1080                1085 tac ttt gat att gtg aag agc ccc atg gat ctt tct acc att aag agg    4511
Tyr Phe Asp Ile Val Lys Ser Pro Met Asp Leu Ser Thr Ile Lys Arg
1090                1095                1100 aag tta gac act gga cag tat cag gag ccc tgg cag tat gtc gat gat    4559
Lys Leu Asp Thr Gly Gln Tyr Gln Glu Pro Trp Gln Tyr Val Asp Asp
1105                1110                1115                1120 att tgg ctt atg ttc aat aat gcc tgg tta tat aac cgg aaa aca tca    4607
Ile Trp Leu Met Phe Asn Asn Ala Trp Leu Tyr Asn Arg Lys Thr Ser
            1125                1130                1135 cgg gta tac aaa tac tgc tcc aag ctc tct gag gtc ttt gaa caa gaa    4655
Arg Val Tyr Lys Tyr Cys Ser Lys Leu Ser Glu Val Phe Glu Gln Glu
                1140                1145                1150 att gac cca gtg atg caa agc ctt gga tac tgt tgt ggc aga aag ttg    4703
Ile Asp Pro Val Met Gln Ser Leu Gly Tyr Cys Cys Gly Arg Lys Leu
        1155                1160                1165 gag ttc tct cca cag aca ctg tgt tgc tac ggc aaa cag ttg tgc aca    4751
Glu Phe Ser Pro Gln Thr Leu Cys Cys Tyr Gly Lys Gln Leu Cys Thr
    1170                1175                1180 ata cct cgt gat gcc act tat tac agt tac cag aac agg tat cat ttc    4799
Ile Pro Arg Asp Ala Thr Tyr Tyr Ser Tyr Gln Asn Arg Tyr His Phe
1185                1190                1195                1200 tgt gag aag tgt ttc aat gag atc caa ggg gag agc gtt tct ttg ggg    4847
Cys Glu Lys Cys Phe Asn Glu Ile Gln Gly Glu Ser Val Ser Leu Gly
            1205                1210                1215 gat gac cct tcc cag cct caa act aca ata aat aaa gaa caa ttt tcc    4895
Asp Asp Pro Ser Gln Pro Gln Thr Thr Ile Asn Lys Glu Gln Phe Ser
                1220                1225                1230 aag aga aaa aat gac aca ctg gat cct gaa ctg ttt gtt gaa tgt aca    4943
Lys Arg Lys Asn Asp Thr Leu Asp Pro Glu Leu Phe Val Glu Cys Thr
        1235                1240                1245 gag tgc gga aga aag atg cat cag atc tgt gtc ctt cac cat gag atc    4991
Glu Cys Gly Arg Lys Met His Gln Ile Cys Val Leu His His Glu Ile
    1250                1255                1260 atc tgg cct gct gga ttc gtc tgt gat ggc tgt tta aag aaa agt gca    5039
Ile Trp Pro Ala Gly Phe Val Cys Asp Gly Cys Leu Lys Lys Ser Ala
1265                1270                1275                1280 cga act agg aaa gaa aat aag ttt tct gct aaa agg ttg cca tct acc    5087
Arg Thr Arg Lys Glu Asn Lys Phe Ser Ala Lys Arg Leu Pro Ser Thr
            1285                1290                1295 aga ctt ggc acc ttt cta gag aat cgt gtg aat gac ttt ctg agg cga    5135
Arg Leu Gly Thr Phe Leu Glu Asn Arg Val Asn Asp Phe Leu Arg Arg
                1300                1305                1310 cag aat cac cct gag tca gga gag gtc act gtt aga gta gtt cat gct    5183
Gln Asn His Pro Glu Ser Gly Glu Val Thr Val Arg Val Val His Ala
        1315                1320                1325 tct gac aaa acc gtg gaa gta aaa cca ggc atg aaa gca agg ttt gtg    5231
Ser Asp Lys Thr Val Glu Val Lys Pro Gly Met Lys Ala Arg Phe Val
    1330                1335                1340 gac agt gga gag atg gca gaa tcc ttt cca tac cga acc aaa gcc ctc    5279
Asp Ser Gly Glu Met Ala Glu Ser Phe Pro Tyr Arg Thr Lys Ala Leu
1345                1350                1355                1360 ttt gcc ttt gaa gaa att gat ggt gtt gac ctg tgc ttc ttt ggc atg    5327
Phe Ala Phe Glu Glu Ile Asp Gly Val Asp Leu Cys Phe Phe Gly Met
            1365                1370                1375 cat gtt caa gag tat ggc tct gac tgc cct cca ccc aac cag agg aga    5375
```

```
His Val Gln Glu Tyr Gly Ser Asp Cys Pro Pro Pro Asn Gln Arg Arg
            1380                1385                1390 gta tac ata tct tac ctc gat agt gtt cat ttc ttc cgt cct aaa tgc    5423
Val Tyr Ile Ser Tyr Leu Asp Ser Val His Phe Phe Arg Pro Lys Cys
        1395                1400                1405 ttg agg act gca gtc tat cat gaa atc cta att gga tat tta gaa tat    5471
Leu Arg Thr Ala Val Tyr His Glu Ile Leu Ile Gly Tyr Leu Glu Tyr
    1410                1415                1420 gtc aag aaa tta ggt tac aca aca ggg cat att tgg gca tgt cca cca    5519
Val Lys Lys Leu Gly Tyr Thr Thr Gly His Ile Trp Ala Cys Pro Pro
1425                1430                1435                1440 agt gag gga gat gat tat atc ttc cat tgc cat cct cct gac cag aag    5567
Ser Glu Gly Asp Asp Tyr Ile Phe His Cys His Pro Pro Asp Gln Lys
            1445                1450                1455 ata ccc aag ccc aag cga ctg cag gaa tgg tac aaa aaa atg ctt gac    5615
Ile Pro Lys Pro Lys Arg Leu Gln Glu Trp Tyr Lys Lys Met Leu Asp
        1460                1465                1470 aag gct gta tca gag cgt att gtc cat gac tac aag gat att ttt aaa    5663
Lys Ala Val Ser Glu Arg Ile Val His Asp Tyr Lys Asp Ile Phe Lys
    1475                1480                1485 caa gct act gaa gat aga tta aca agt gca aag gaa ttg cct tat ttc    5711
Gln Ala Thr Glu Asp Arg Leu Thr Ser Ala Lys Glu Leu Pro Tyr Phe
    1490                1495                1500 gag ggt gat ttc tgg ccc aat gtt ctg gaa gaa agc att aag gaa ctg    5759
Glu Gly Asp Phe Trp Pro Asn Val Leu Glu Glu Ser Ile Lys Glu Leu
1505                1510                1515                1520 gaa cag gag gaa gaa gag aga aaa cga gag gaa aac acc agc aat gaa    5807
Glu Gln Glu Glu Glu Glu Arg Lys Arg Glu Glu Asn Thr Ser Asn Glu
            1525                1530                1535 agc aca gat gtg acc aag gga gac agc aaa aat gct aaa aag aag aat    5855
Ser Thr Asp Val Thr Lys Gly Asp Ser Lys Asn Ala Lys Lys Lys Asn
        1540                1545                1550 aat aag aaa acc agc aaa aat aag agc agc ctg agt agg ggc aac aag    5903
Asn Lys Lys Thr Ser Lys Asn Lys Ser Ser Leu Ser Arg Gly Asn Lys
    1555                1560                1565 aag aaa ccc ggg atg ccc aat gta tct aac gac ctc tca cag aaa cta    5951
Lys Lys Pro Gly Met Pro Asn Val Ser Asn Asp Leu Ser Gln Lys Leu
    1570                1575                1580 tat gcc acc atg gag aag cat aaa gag gtc ttc ttt gtg atc cgc ctc    5999
Tyr Ala Thr Met Glu Lys His Lys Glu Val Phe Phe Val Ile Arg Leu
1585                1590                1595                1600 att gct ggc cct gct gcc aac tcc ctg cct ccc att gtt gat cct gat    6047
Ile Ala Gly Pro Ala Ala Asn Ser Leu Pro Pro Ile Val Asp Pro Asp
            1605                1610                1615 cct ctc atc ccc tgc gat ctg atg gat ggt cgg gat gcg ttt ctc acg    6095
Pro Leu Ile Pro Cys Asp Leu Met Asp Gly Arg Asp Ala Phe Leu Thr
        1620                1625                1630 ctg gca agg gac aag cac ctg gag ttc tct tca ctc cga aga gcc cag    6143
Leu Ala Arg Asp Lys His Leu Glu Phe Ser Ser Leu Arg Arg Ala Gln
    1635                1640                1645 tgg tcc acc atg tgc atg ctg gtg gag ctg cac acg cag agc cag gac    6191
Trp Ser Thr Met Cys Met Leu Val Glu Leu His Thr Gln Ser Gln Asp
    1650                1655                1660 cgc ttt gtc tac acc tgc aat gaa tgc aag cac cat gtg gag aca cgc    6239
Arg Phe Val Tyr Thr Cys Asn Glu Cys Lys His His Val Glu Thr Arg
1665                1670                1675                1680 tgg cac tgt act gtc tgt gag gat tat gac ttg tgt atc acc tgc tat    6287
Trp His Cys Thr Val Cys Glu Asp Tyr Asp Leu Cys Ile Thr Cys Tyr
            1685                1690                1695 aac act aaa aac cat gac cac aaa atg gag aaa cta ggc ctt ggc tta    6335
```

```
                    -continued
Asn Thr Lys Asn His Asp His Lys Met Glu Lys Leu Gly Leu Gly Leu
        1700               1705                1710 gat gat gag agc aac aac cag cag gct gca gcc acc cag agc cca ggc      6383
Asp Asp Glu Ser Asn Asn Gln Gln Ala Ala Ala Thr Gln Ser Pro Gly
         1715                1720               1725 gat tct cgc cgc ctg agt atc cag cgc tgc atc cag tct ctg gtc cat      6431
Asp Ser Arg Arg Leu Ser Ile Gln Arg Cys Ile Gln Ser Leu Val His
    1730                1735                1740 gct tgc cag tgt cgg aat gcc aat tgc tca ctg cca tcc tgc cag aag      6479
Ala Cys Gln Cys Arg Asn Ala Asn Cys Ser Leu Pro Ser Cys Gln Lys
1745                1750                1755                1760 atg aag cgg gtt gtg cag cat acc aag ggt tgc aaa cgg aaa acc aat      6527
Met Lys Arg Val Val Gln His Thr Lys Gly Cys Lys Arg Lys Thr Asn
             1765                1770                1775 ggc ggg tgc ccc atc tgc aag cag ctc att gcc ctc tgc tgc tac cat      6575
Gly Gly Cys Pro Ile Cys Lys Gln Leu Ile Ala Leu Cys Cys Tyr His
         1780                1785                1790 gcc aag cac tgc cag gag aac aaa tgc ccg gtg ccg ttc tgc cta aac      6623
Ala Lys His Cys Gln Glu Asn Lys Cys Pro Val Pro Phe Cys Leu Asn
    1795                1800                1805 atc aag cag aag ctc cgg cag caa cag ctg cag cac cga cta cag cag      6671
Ile Lys Gln Lys Leu Arg Gln Gln Gln Leu Gln His Arg Leu Gln Gln
1810                1815                1820 gcc caa atg ctt cgc agg agg atg gcc agc atg cag cgg act ggt gtg      6719
Ala Gln Met Leu Arg Arg Arg Met Ala Ser Met Gln Arg Thr Gly Val
1825                1830                1835                1840 gtt ggg cag caa cag ggc ctc cct tcc ccc act cct gcc act cca acg      6767
Val Gly Gln Gln Gln Gly Leu Pro Ser Pro Thr Pro Ala Thr Pro Thr
             1845                1850                1855 aca cca act ggc caa cag cca acc acc ccg cag acg ccc cag ccc act      6815
Thr Pro Thr Gly Gln Gln Pro Thr Thr Pro Gln Thr Pro Gln Pro Thr
         1860                1865                1870 tct cag cct cag cct acc cct ccc aat agc atg cca ccc tac ttg ccc      6863
Ser Gln Pro Gln Pro Thr Pro Pro Asn Ser Met Pro Pro Tyr Leu Pro
    1875                1880                1885 agg act caa gct gct ggc cct gtg tcc cag ggt aag gca gca ggc cag      6911
Arg Thr Gln Ala Ala Gly Pro Val Ser Gln Gly Lys Ala Ala Gly Gln
1890                1895                1900 gtg acc cct cca acc cct cct cag act gct cag cca ccc ctt cca ggg      6959
Val Thr Pro Pro Thr Pro Pro Gln Thr Ala Gln Pro Pro Leu Pro Gly
1905                1910                1915                1920 ccc cca cct aca gca gtg gaa atg gca atg cag att cag aga gca gcg      7007
Pro Pro Pro Thr Ala Val Glu Met Ala Met Gln Ile Gln Arg Ala Ala
             1925                1930                1935 gag acg cag cgc cag atg gcc cac gtg caa att ttt caa agg cca atc      7055
Glu Thr Gln Arg Gln Met Ala His Val Gln Ile Phe Gln Arg Pro Ile
         1940                1945                1950 caa cac cag atg ccc ccg atg act ccc atg gcc ccc atg ggt atg aac      7103
Gln His Gln Met Pro Pro Met Thr Pro Met Ala Pro Met Gly Met Asn
    1955                1960                1965 cca cct ccc atg acc aga ggt ccc agt ggg cat ttg gag cca ggg atg      7151
Pro Pro Pro Met Thr Arg Gly Pro Ser Gly His Leu Glu Pro Gly Met
1970                1975                1980 gga ccg aca ggg atg cag caa cag cca ccc tgg agc caa gga gga ttg      7199
Gly Pro Thr Gly Met Gln Gln Gln Pro Pro Trp Ser Gln Gly Gly Leu
1985                1990                1995                2000 cct cag ccc cag caa cta cag tct ggg atg cca agg cca gcc atg atg      7247
Pro Gln Pro Gln Gln Leu Gln Ser Gly Met Pro Arg Pro Ala Met Met
             2005                2010                2015 tca gtg gcc cag cat ggt caa cct ttg aac atg gct cca caa cca gga      7295
```

```
Ser Val Ala Gln His Gly Gln Pro Leu Asn Met Ala Pro Gln Pro Gly
        2020                2025                2030 ttg ggc cag gta ggt atc agc cca ctc aaa cca ggc act gtg tct caa    7343
Leu Gly Gln Val Gly Ile Ser Pro Leu Lys Pro Gly Thr Val Ser Gln
        2035                2040                2045 caa gcc tta caa aac ctt ttg cgg act ctc agg tct ccc agc tct ccc    7391
Gln Ala Leu Gln Asn Leu Leu Arg Thr Leu Arg Ser Pro Ser Ser Pro
    2050                2055                2060 ctg cag cag caa cag gtg ctt agt atc ctt cac gcc aac ccc cag ctg    7439
Leu Gln Gln Gln Gln Val Leu Ser Ile Leu His Ala Asn Pro Gln Leu
2065                2070                2075                2080 ttg gct gca ttc atc aag cag cgg gct gcc aag tat gcc aac tct aat    7487
Leu Ala Ala Phe Ile Lys Gln Arg Ala Ala Lys Tyr Ala Asn Ser Asn
        2085                2090                2095 cca caa ccc atc cct ggg cag cct ggc atg ccc cag ggg cag cca ggg    7535
Pro Gln Pro Ile Pro Gly Gln Pro Gly Met Pro Gln Gly Gln Pro Gly
        2100                2105                2110 cta cag cca cct acc atg cca ggt cag cag ggg gtc cac tcc aat cca    7583
Leu Gln Pro Pro Thr Met Pro Gly Gln Gln Gly Val His Ser Asn Pro
        2115                2120                2125 gcc atg cag aac atg aat cca atg cag gcg ggc gtt cag agg gct ggc    7631
Ala Met Gln Asn Met Asn Pro Met Gln Ala Gly Val Gln Arg Ala Gly
    2130                2135                2140 ctg ccc cag cag caa cca cag cag caa ctc cag cca ccc atg gga ggg    7679
Leu Pro Gln Gln Gln Pro Gln Gln Gln Leu Gln Pro Pro Met Gly Gly
2145                2150                2155                2160 atg agc ccc cag gct cag cag atg aac atg aac cac aac acc atg cct    7727
Met Ser Pro Gln Ala Gln Gln Met Asn Met Asn His Asn Thr Met Pro
        2165                2170                2175 tca caa ttc cga gac atc ttg aga cga cag caa atg atg caa cag cag    7775
Ser Gln Phe Arg Asp Ile Leu Arg Arg Gln Gln Met Met Gln Gln Gln
        2180                2185                2190 cag caa cag gga gca ggg cca gga ata ggc cct gga atg gcc aac cat    7823
Gln Gln Gln Gly Ala Gly Pro Gly Ile Gly Pro Gly Met Ala Asn His
        2195                2200                2205 aac cag ttc cag caa ccc caa gga gtt ggc tac cca cca cag ccg cag    7871
Asn Gln Phe Gln Gln Pro Gln Gly Val Gly Tyr Pro Pro Gln Pro Gln
        2210                2215                2220 cag cgg atg cag cat cac atg caa cag atg caa caa gga aat atg gga    7919
Gln Arg Met Gln His His Met Gln Gln Met Gln Gln Gly Asn Met Gly
2225                2230                2235                2240 cag ata ggc cag ctt ccc cag gcc ttg gga gca gag gca ggt gcc agt    7967
Gln Ile Gly Gln Leu Pro Gln Ala Leu Gly Ala Glu Ala Gly Ala Ser
        2245                2250                2255 cta cag gcc tat cag cag cga ctc ctt cag caa cag atg ggg tcc cct    8015
Leu Gln Ala Tyr Gln Gln Arg Leu Leu Gln Gln Gln Met Gly Ser Pro
        2260                2265                2270 gtt cag ccc aac ccc atg agc ccc cag cag cat atg ctc cca aat cag    8063
Val Gln Pro Asn Pro Met Ser Pro Gln Gln His Met Leu Pro Asn Gln
        2275                2280                2285 gcc cag tcc cca cac cta caa ggc cag cag atc cct aat tct ctc tcc    8111
Ala Gln Ser Pro His Leu Gln Gly Gln Gln Ile Pro Asn Ser Leu Ser
        2290                2295                2300 aat caa gtg cgc tct ccc cag cct gtc cct tct cca cgg cca cag tcc    8159
Asn Gln Val Arg Ser Pro Gln Pro Val Pro Ser Pro Arg Pro Gln Ser
2305                2310                2315                2320 cag ccc ccc cac tcc agt cct tcc cca agg atg cag cct cag cct tct    8207
Gln Pro Pro His Ser Ser Pro Ser Pro Arg Met Gln Pro Gln Pro Ser
        2325                2330                2335 cca cac cac gtt tcc cca cag aca agt tcc cca cat cct gga ctg gta    8255
```

-continued

```
Pro His His Val Ser Pro Gln Thr Ser Ser Pro His Pro Gly Leu Val
        2340                2345                2350 gct gcc cag gcc aac ccc atg gaa caa ggg cat ttt gcc agc ccg gac    8303
Ala Ala Gln Ala Asn Pro Met Glu Gln Gly His Phe Ala Ser Pro Asp
        2355                2360                2365 cag aat tca atg ctt tct cag ctt gct agc aat cca ggc atg gca aac    8351
Gln Asn Ser Met Leu Ser Gln Leu Ala Ser Asn Pro Gly Met Ala Asn
    2370                2375                2380 ctc cat ggt gca agc gcc acg gac ctg gga ctc agc acc gat aac tca    8399
Leu His Gly Ala Ser Ala Thr Asp Leu Gly Leu Ser Thr Asp Asn Ser
    2385                2390                2395                2400 gac ttg aat tca aac ctc tca cag agt aca cta gac ata cac              8441
Asp Leu Asn Ser Asn Leu Ser Gln Ser Thr Leu Asp Ile His
                2405                2410 tagagacacc ttgtatttgg ggagcaaaaa aattattttc tcttaacaag actttttgta    8501
ctgaaaacaa tttttttgaa tctttcgtag cctaaaagac aatttttcctt ggaacacata   8561 agaactgtgc agtagccgtt tgtggtttaa agcaaacatg caagatgaac ctgagggatg   8621
atagaataca agaatatat ttttgttatg ggctggttac caccagcctt tcttcccctt    8681
tgtgtgtgtg gttcaagtgt gcactgggag gaggctgagg cctgtgaagc caaacaatat   8741
gctcctgcct tgcacctcca ataggtttta ttattttttt taaattaatg aacatatgta   8801
atattaatga acatatgtaa tattaatagt tattatttac tggtgcagat ggttgacatt   8861
tttccctatt ttcctcactt tatggaagag ttaaaacatt tctaaccag aggacaaaag    8921 gggtaatgt tactttgaaa ttacattcta tatatatata aatatatata aatatatatt    8981
aaaataccag ttttttttct ctgggtgcaa agatgttcat tcttttaaaa aatgtttaaa   9041
aaaaa                                                              9046
```

<210> SEQ ID NO 2
<211> LENGTH: 5443
<212> TYPE: DNA
<213> ORGANISM: Mus musculus
<220> FEATURE:
<221> NAME/KEY: promoter
<222> LOCATION: (1)..(5443)

<400> SEQUENCE: 2

```
ggatcctgca aggtcacaca agggtctcca cccaccaggt gccctagtct caatttcagt     60
ttccatgcct tgttctcaca atgctggcct ccccagagct aatttggact ttgttttat    120 ttcaaaaggg cctgaatgag gagtagatct tgtgctaccc agctctaagg gtgcccgtga   180
agccctcaga cctggagcct ttgcaacagc ccttaggtg gaagcagaat aaagcaattt    240
tccttaaagc caaaatcctg cctctagact cttcttctct gacctcggtc cctgggctct   300
agggtgggga ggtggggctt ggaagaagaa ggtggggaag tggcaaaagc cgatccctag   360
ggccctgtga agttcggagc cttccctgta cagcactggc tcatagatcc tcctccagcc   420
aaacatagca agaagtgata cctcctttgt gacttcccca ggcccagtac ctgtcaggtt   480
gaaacaggat ttagagaagc ctctgaactc acctgaactc tgaagctcat ccaccaagca   540
agcacctagg tgccactgct agttagtatc ctacgctgat aatatgcaga gctgggccac   600
agaagtcctg gggtgtagga actgaccagt gacttttcag tcggcaaagg tatgacccc    660 tcagcagatg tagtaatgtc cccttagatc ccatcccagg caggtctcta agaggacatg   720
ggatgagaga tgtagtcatg tggcattcca aacacagcta tccacagtgt cccttgcccc   780
ttccacttag ccaggaggac agtaaccttg gcctatcttt cttcctcccc atcctcccag   840
```

```
gacacacccc ctggtctgca gtattcattt cttccttcac gtccctctg tgacttccat    900
ttgcaaggct tttgacctct gcagctgctg aagatagag tttggccta ggtgtggcaa    960
gccatctcaa gagaaagcag acaacagggg accagattt tggaaggatc aggaactaaa  1020
tcactggcgg gcctgggggt agaaaaaaga gtgagtgagt ccgctccagc taagccaagc  1080
tagtccccga gatactctgc cacagctggg ctgctcgggg tagctttagg aatgtgggtc  1140
tgaaagacaa tgggattgga agacatctct ttgagtctcc cctcaacccc acctacagac  1200
acactcgtgt gtggccagac tcctgttcaa cagccctctg tgttctgacc actgagctag  1260
gcaaccagag catgggccct gtgctgagga tgaagagttg gttaccaata gcaaaaacag  1320
caggggaggg agaacagaga acgaaataag gaaggaagaa ggaaaggcca gtcaatcaga  1380
tgcagtcaga agagatggga agccaacaca cagcttgagc agaggaaaca gaaaagggag  1440
agattctggg cataaggagg ccacagaaag aagagcccag gccccccaag tctcctcttt  1500
ataccctcat cccgtctccc aattaagccc actcttcttc ctagatcaga cctgagctgc  1560
agcgaagaga cccgtaggga ggatcacact ggatgaagga gatgtgtgga gaagtccagg  1620
gcaacctaag agccagagcc taaaagagca agagataaag gtgcttcaaa ggtgccagg   1680
ctgtgcacac agagggtcga ggactggtgg tagagcctca agataaggat gatgctcaga  1740
atgggcgggg gggggattc tggggggggg agagagaagg tgagaaggag cctgaacag   1800
agaatctgga agcgctggaa acgataccat aaagggaaga acccaggcta cctttagatg  1860
taaatcatga agacaggga gaagggaagc tggagagagt agaaggaccc cggggcaaga   1920
catggaagca aggacaagcc aggttgagcg ctccgtgaaa tcagcctgct gaaggcagag  1980
ccctggtatg agcaccagaa cagcagaggc tagggttaat gtcgagacag gaacagaag   2040
gtagacacag gaacagacag agacggggga gccaggtaac aaaggaatgg tccttctcac  2100
ctgtggccag agcgtccatc tgtgtccaca tactctagaa tgttcatcag actgcagggc  2160
tggcttggga ggcagctgga aagagtatgt gagagccagg ggagacaagg gggcctagga  2220
aaggaagaag agggcaaacc aggccacaca agagggcaga gcccagaact gagttaactc  2280
cttccttgtt gcatcttcca taggaggcag tgggaactct gtgaccacca tcccccatga  2340
gcccccacta cccataccaa gtttggcctg agtggcattc taggttccct gaggacagag  2400
cctggccttt gtctcttgga cctgacccaa gctgacccaa tgttctcagt accttatcat  2460
gccctcaaga gcttgagaac caggcagtga catattaggc catgggctaa ccctggagct  2520
tgcacacagg agcctcaagt gacctccagg gacacagctg cagacaggtg gcctttatcc  2580
ccaaagagca accatttggc ataggtggct gcaaatggga atgcaaggtt gaatcaggtc  2640
ccttcaagaa tactgcatgc aagacctaag acccctggag agaggggtat gctcctgccc  2700
ccacccacca taaggggagt gaactatcct aggggctgg cgaccttggg gagacaccac   2760
attactgaga gtgctgagcc cagaaaaact gaccgccctg tgtcctgccc acctccacac  2820
tctagagcta tattgagagg tgacagtaga tagggtggga gctggtagca gggagagtgt  2880
tcctgggtgt gagggtgtag gggaaagcca gagcagggga gtctggcttt gtctcctgaa  2940
cacaatgtct acttagttat aacaggcatg acctgctaaa gacccaacat ctacgacctc  3000
tgaaaagaca gcagccctgg aggacagggg ttgtctctga gccttgggtg cttgatggtg  3060
ccacaaagga gggcatgagt gtgagtataa ggccccagga gcgttagaga agggcacttg  3120
ggaaggggtc agtctgcaga gccctatcc atggaatctg gagcctgggg ccaactggtg   3180
taaatctctg ggcctgccag gcattcaaag cagcacctgc atcctctggc agcctgggga  3240
```

```
ggcggaaggg agcaaccccc cacttatacc ctttctccct cagccccagg attaacacct    3300
ctggccttcc cccttcccac ctcccatcag gagtggaggg ttgcagaggg agggtaaaaa    3360
cctacatgtc caaacatcat ggtgcacgat atatggatca gtatgtgtag aggcaagaaa    3420
ggaaatctgc aggcttaact gggttaatgt gtaaagtctg tgtgcatgtg tgtgtgtctg    3480
actgaaaacg ggcatggctg tgcagctgtt cagttctgtg cgtgaggtta ccagactgca    3540
ggtttgtgtg taaattgccc aaggcaaagt gggtgaatcc cttccatggt ttaaagagat    3600
tggatgatgg cctgcatctc aaggaccatg gaaaatagaa tggacactct atatgtgtct    3660
ctaagctaag gtagcaaggt ctttggagga cacctgtcta gagatgtggg caacagagac    3720
tacagacagt atctgtacag agtaaggaga gagaggaggg ggtgtagaat tctcttacta    3780
tcaaagggaa actgagtcgt gcacctgcaa agtggatgct ctccctagac atcatgactt    3840
tgtctctggg gagccagcac tgtggaactt caggtctgag agagtaggag gctcccctca    3900
gcctgaagct atgcagatag ccaggggttga aaggggggaag ggagagcctg ggatgggagc    3960
ttgtgtgttg gaggcagggg acagatatta agcctggaag agaaggtgac ccttacccag    4020
ttgttcaact caccccttcag attaaaaata actgaggtaa gggcctgggt aggggaggtg    4080
gtgtgagacg ctcctgtctc tcctctatct gcccatcggc cctttgggga ggaggaatgt    4140
gcccaaggac taaaaaaagg ccatggagcc agaggggcga gggcaacaga cctttcatgg    4200
gcaaaccttg gggccctgct gtcctcctgt cacctccaga gccaagggat caaaggagga    4260
ggagccagga caggagggaa gtgggaggga gggtcccagc agaggactcc aaatttaggc    4320
agcaggcata tgggatggga tataaagggg ctggagcact gagagctgtc agagatttct    4380
ccaacccagg taagagggag tttcgggtgg gggctcttca cccacaccag acctctcccc    4440
acctagaagg aaactgcctt tcctggaagt gggggttcagg ccggtcagag atctgacagg    4500
gtggccttcc accagcctgg gaagttctca gtggcaggag gttttccacaa gaaacactgg    4560
atgccccttc ccttacgctg tcttctccat cttcctcctg gggatgctcc tccccgtctt    4620
ggtttatctt ggctcttcgt cttcagcaag atttgccctg tgctgtccac tccatctttc    4680
tctactgtct ccgtgccttg ccttgccttc ttgcgtgtcc ttccttttcca cccatttctc    4740
acttcacctt ttctcccctt ctcatttgta ttcatccttc cttccttcct tccttccttc    4800
cttccttcct tccttccttc ctttctccct tccttccttc cttccttcct tccttccttc    4860
cttccttcct gtgtcagagt gctgagaatc acacctgggg ttcccaccct tatgtaaaca    4920
atcttccagt gagccacagc ttcagtgctg ctgggtgctc tcttaccttc ctcaccccct    4980
ggcttgtcct gttccatcct ggtcaggatc tctagattgg tctcccagcc tctgctactc    5040
ctcttcctgc ctgttcctct ctctgtccag ctgcgccact gtggtgcctc gttccagctg    5100
tggtccacat tcttcaggat tctctgaaaa gttaaccagg tgagaatgtt tcccctgtag    5160
acagcagatc acgattctcc cggaagtcag gcttccagcc ctctctttct ctgcccagct    5220
gcccggcact cttagcaaac ctcaggcacc cttacccccac atagacctct gacagagaag    5280
caggcacttt acatggagtc ctggtgggag agccataggc tacggtgtaa aagaggcagg    5340
gaagtggtgg tgtaggaaag tcaggacttc acatagaagc ctagcccaca ccagaaatga    5400
cagacagatc cctcctatct cccccataag agtttgagtc gac                      5443
```

<210> SEQ ID NO 3
<211> LENGTH: 20
<212> TYPE: DNA
<213> ORGANISM: Artificial Sequence
<220> FEATURE:

```
<223> OTHER INFORMATION: Sense Primer using in PCR of Example 1

<400> SEQUENCE: 3
tcttagcaaa cctcaggcac                                          20

<210> SEQ ID NO 4
<211> LENGTH: 20
<212> TYPE: DNA
<213> ORGANISM: Artificial Sequence
<220> FEATURE:
<223> OTHER INFORMATION: Antisense Primer using in PCR of Example 1

<400> SEQUENCE: 4 ccaccattggttagtcccaa                                           20

<210> SEQ ID NO 5
<211> LENGTH: 20
<212> TYPE: DNA
<213> ORGANISM: Artificial Sequence
<220> FEATURE:
<223> OTHER INFORMATION: Sense Primer using in PCR of Example 2

<400> SEQUENCE: 5 gcaacaggtgcttagtatcc                                           20

<210> SEQ ID NO 6
<211> LENGTH: 20
<212> TYPE: DNA
<213> ORGANISM: Artificial Sequence
<220> FEATURE:
<223> OTHER INFORMATION: Antisense Primer using in PCR of Example 2

<400> SEQUENCE: 6
ctgttgcatg tgatgctgca                                          20
```